US010524508B2

(12) United States Patent
Sur et al.

(10) Patent No.: US 10,524,508 B2
(45) Date of Patent: Jan. 7, 2020

(54) INDUCTION-BASED AEROSOL DELIVERY DEVICE

(71) Applicant: RAI Strategic Holdings, Inc., Winston-Salem, NC (US)

(72) Inventors: Rajesh Sur, Winston-Salem, NC (US); James W. Rogers, Winston-Salem, NC (US); Stephen B. Sears, Siler City, NC (US); Eric T. Hunt, Pfafftown, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 495 days.

(21) Appl. No.: 15/352,153

(22) Filed: Nov. 15, 2016

(65) Prior Publication Data

US 2018/0132531 A1     May 17, 2018

(51) Int. Cl.
*A24F 47/00*     (2006.01)
*A61M 15/06*    (2006.01)
(Continued)

(52) U.S. Cl.
CPC ........... *A24F 47/008* (2013.01); *H01G 11/06* (2013.01); *H01M 10/0525* (2013.01);
(Continued)

(58) Field of Classification Search
None
See application file for complete search history.

(56) References Cited

U.S. PATENT DOCUMENTS

| | | |
|---|---|---|
| 1,771,366 A | 7/1930 | Wyss et al. |
| 2,057,353 A | 10/1936 | Whittemore, Jr. |

(Continued)

FOREIGN PATENT DOCUMENTS

| | | |
|---|---|---|
| AU | 276250 | 7/1965 |
| CA | 2 641 869 | 5/2010 |

(Continued)

OTHER PUBLICATIONS

"bq500212A Low System Cost, Wireless Power Controller for WPC TX A5 or A11", Texas Instruments, SLUSBD6D, Jul. 2013, pp. 1-29, Revised Jul. 2016.
"bq51013B Highly Integrated Wireless Receiver Qi (WPC v1.1) Compliant Power Supply", Texas Instruments, SLUSB62B, Mar. 2013, pp. 1-47, Revised Aug. 2015.
"Qi Compliant Wireless Power Transmitter Manager", Texas Instruments, SLUSAL8C, Jun. 2011, pp. 1-24, Revised Sep. 2012.

(Continued)

*Primary Examiner* — Thor S Campbell
(74) *Attorney, Agent, or Firm* — Womble Bond Dickinson (US) LLP

(57) ABSTRACT

An aerosol delivery device is provided that includes a substrate configured to carry an aerosol precursor composition, and a resonant transformer including a transmitter coupling device and a resonant receiver coupling device that is positioned in proximity to the substrate. The aerosol delivery device also includes a pulse width modulation (PWM) inverter configured to drive the resonant transformer. The PWM inverter includes a bridge circuit coupled to the transmitter coupling device, and a PWM controller embodied as an integrated circuit and configured to output a PWM signal to the bridge circuit configured to drive the transmitter coupling device to generate an oscillating magnetic field and induce an alternating voltage in the resonant receiver coupling device when exposed to the oscillating magnetic field. The alternating voltage causes the resonant receiver coupling device to generate heat and thereby vaporize components of the aerosol precursor composition.

20 Claims, 12 Drawing Sheets

(51) Int. Cl.
*H01G 11/06* (2013.01)
*H01M 10/0525* (2010.01)
*H05B 1/02* (2006.01)

(52) U.S. Cl.
CPC ....... *H05B 1/0244* (2013.01); *H01M 2220/30* (2013.01); *H05B 2206/024* (2013.01)

(56) References Cited

U.S. PATENT DOCUMENTS

| | | |
|---|---|---|
| 2,104,266 A | 1/1938 | McCormick |
| 3,200,819 A | 8/1965 | Gilbert |
| 4,284,089 A | 8/1981 | Ray |
| 4,303,083 A | 12/1981 | Burruss, Jr. |
| 4,735,217 A | 4/1988 | Gerth et al. |
| 4,848,374 A | 7/1989 | Chard et al. |
| 4,907,606 A | 3/1990 | Lilja et al. |
| 4,922,901 A | 5/1990 | Brooks et al. |
| 4,945,931 A | 8/1990 | Gori |
| 4,947,874 A | 8/1990 | Brooks et al. |
| 4,947,875 A | 8/1990 | Brooks et al. |
| 4,986,286 A | 1/1991 | Roberts et al. |
| 5,019,122 A | 5/1991 | Clearman |
| 5,042,510 A | 8/1991 | Curtiss et al. |
| 5,060,671 A | 10/1991 | Counts et al. |
| 5,093,894 A | 3/1992 | Deevi et al. |
| 5,144,962 A | 9/1992 | Counts et al. |
| 5,249,586 A | 10/1993 | Morgan et al. |
| 5,261,424 A | 11/1993 | Sprinkel, Jr. |
| 5,322,075 A | 6/1994 | Deevi et al. |
| 5,353,813 A | 10/1994 | Deevi et al. |
| 5,369,723 A | 11/1994 | Counts et al. |
| 5,372,148 A | 12/1994 | McCafferty et al. |
| 5,388,574 A | 2/1995 | Ingebrethsen et al. |
| 5,408,574 A | 4/1995 | Deevi et al. |
| 5,468,936 A | 11/1995 | Deevi et al. |
| 5,498,850 A | 3/1996 | Das |
| 5,515,842 A | 5/1996 | Ramseyer et al. |
| 5,530,225 A | 6/1996 | Hajaligol |
| 5,564,442 A | 10/1996 | MacDonald et al. |
| 5,613,505 A | 3/1997 | Campbell et al. |
| 5,649,554 A | 7/1997 | Sprinkel et al. |
| 5,666,977 A | 9/1997 | Higgins et al. |
| 5,687,746 A | 11/1997 | Rose et al. |
| 5,726,421 A | 3/1998 | Fleischhauer et al. |
| 5,727,571 A | 3/1998 | Meiring et al. |
| 5,743,251 A | 4/1998 | Howell et al. |
| 5,799,663 A | 9/1998 | Gross et al. |
| 5,819,756 A | 10/1998 | Mielordt |
| 5,865,185 A | 2/1999 | Collins et al. |
| 5,865,186 A | 2/1999 | Volsey, II |
| 5,878,752 A | 3/1999 | Adams et al. |
| 5,894,841 A | 4/1999 | Voges |
| 5,934,289 A | 8/1999 | Watkins et al. |
| 5,954,979 A | 9/1999 | Counts et al. |
| 5,967,148 A | 10/1999 | Harris et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,125,853 A | 10/2000 | Susa et al. |
| 6,155,268 A | 12/2000 | Takeuchi |
| 6,164,287 A | 12/2000 | White |
| 6,196,218 B1 | 3/2001 | Voges |
| 6,196,219 B1 | 3/2001 | Hess et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,772,756 B2 | 8/2004 | Shayan |
| 6,803,545 B2 | 10/2004 | Blake et al. |
| 6,803,550 B2 | 10/2004 | Sharpe et al. |
| 6,854,461 B2 | 2/2005 | Nichols |
| 6,854,470 B1 | 2/2005 | Pu |
| 7,117,867 B2 | 10/2006 | Cox et al. |
| 7,185,659 B2 | 3/2007 | Sharpe |
| 7,293,565 B2 | 11/2007 | Griffin et al. |
| 7,513,253 B2 | 4/2009 | Kobayashi et al. |
| 7,775,459 B2 | 8/2010 | Martens, III et al. |
| 7,832,410 B2 | 11/2010 | Hon |
| 7,845,359 B2 | 12/2010 | Montaser |
| 7,896,006 B2 | 3/2011 | Hamano et al. |
| 8,127,772 B2 | 3/2012 | Montaser |
| 8,314,591 B2 | 11/2012 | Terry et al. |
| 8,365,742 B2 | 2/2013 | Hon |
| 8,402,976 B2 | 3/2013 | Fernando et al. |
| 8,499,766 B1 | 8/2013 | Newton |
| 8,528,569 B1 | 9/2013 | Newton |
| 8,550,069 B2 | 10/2013 | Alelov |
| 8,851,081 B2 | 10/2014 | Fernando et al. |
| 9,603,386 B2* | 3/2017 | Xiang .................. A24F 47/008 |
| 9,675,114 B2* | 6/2017 | Timmermans ........ A24F 47/008 |
| 9,808,032 B2* | 11/2017 | Yamada ................ A24F 47/008 |
| 2002/0146242 A1 | 10/2002 | Vieira |
| 2003/0226837 A1 | 12/2003 | Blake et al. |
| 2004/0118401 A1 | 6/2004 | Smith et al. |
| 2004/0129280 A1 | 7/2004 | Woodson et al. |
| 2004/0200488 A1 | 10/2004 | Felter et al. |
| 2004/0226568 A1 | 11/2004 | Takeuchi et al. |
| 2005/0016550 A1 | 1/2005 | Katase |
| 2005/0034723 A1* | 2/2005 | Bennett .................. A61K 9/007 |
| | | 128/203.12 |
| 2006/0016453 A1 | 1/2006 | Kim |
| 2006/0196518 A1 | 9/2006 | Hon |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2008/0038363 A1* | 2/2008 | Zaffaroni ............. A61M 11/041 |
| | | 424/502 |
| 2008/0085103 A1 | 4/2008 | Beland et al. |
| 2008/0092912 A1 | 4/2008 | Robinson et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0095287 A1* | 4/2009 | Emarlou ............. A61M 11/041 |
| | | 128/200.14 |
| 2009/0095311 A1 | 4/2009 | Hon |
| 2009/0095312 A1 | 4/2009 | Herbrich et al. |
| 2009/0126745 A1 | 5/2009 | Hon |
| 2009/0188490 A1 | 7/2009 | Hon |
| 2009/0230117 A1 | 9/2009 | Fernando et al. |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0043809 A1 | 2/2010 | Magnon |
| 2010/0083959 A1 | 4/2010 | Siller |
| 2010/0181387 A1* | 7/2010 | Zaffaroni ............... A61M 15/06 |
| | | 239/13 |
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0090630 A1* | 4/2012 | Hon ...................... A24F 47/002 |
| | | 131/273 |
| 2012/0111347 A1 | 5/2012 | Hon |
| 2012/0132643 A1 | 5/2012 | Choi et al. |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |

(56) References Cited

U.S. PATENT DOCUMENTS

| | | |
|---|---|---|
| 2013/0037041 A1 | 2/2013 | Worm et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0192619 A1 | 8/2013 | Tucker et al. |
| 2013/0199528 A1 | 8/2013 | Goodman et al. |
| 2013/0255702 A1 | 10/2013 | Griffith, Jr. et al. |
| 2013/0284192 A1* | 10/2013 | Peleg .............. A24F 47/002 131/329 |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0060554 A1* | 3/2014 | Collett ............... H05B 3/265 131/328 |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0157583 A1 | 6/2014 | Ward et al. |
| 2014/0209105 A1 | 7/2014 | Sears et al. |
| 2014/0224267 A1* | 8/2014 | Levitz ................ A24F 47/008 131/329 |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2014/0345631 A1 | 11/2014 | Bowen et al. |
| 2015/0007838 A1 | 1/2015 | Fernando et al. |
| 2015/0053217 A1 | 2/2015 | Steingraber et al. |
| 2015/0245669 A1 | 9/2015 | Cadieux et al. |
| 2015/0320116 A1* | 11/2015 | Bleloch ............... A61M 15/06 219/628 |
| 2016/0037826 A1 | 2/2016 | Hearn et al. |
| 2016/0150828 A1* | 6/2016 | Goldstein ........... A24F 47/008 392/387 |
| 2017/0020192 A1* | 1/2017 | Fregonese ......... H05B 3/0014 |
| 2017/0202266 A1* | 7/2017 | Sur ..................... A24F 47/008 |
| 2017/0251719 A1* | 9/2017 | Cyphert ................. A24F 1/00 |
| 2018/0070639 A1* | 3/2018 | Chen ................... A24F 47/008 |
| 2018/0184712 A1* | 7/2018 | Fraser ................. A24F 47/008 |
| 2018/0192700 A1* | 7/2018 | Fraser ................. A24F 47/008 |
| 2019/0124979 A1* | 5/2019 | Sebastian .............. H05B 6/108 |
| 2019/0200677 A1* | 7/2019 | Chong ................. A24F 47/008 |
| 2019/0230987 A1* | 8/2019 | Wu ..................... A24F 47/008 |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 703 735 | 4/1996 |
| EP | 0 845 220 | 6/1998 |
| EP | 1 618 803 | 1/2006 |
| EP | 2 316 286 | 5/2011 |
| GB | 2469850 | 11/2010 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | WO 2013/089551 | 6/2013 |
| WO | 2015176898 A1 | 11/2015 |
| WO | 2015177043 A1 | 11/2015 |
| WO | 2015177044 A1 | 11/2015 |
| WO | 2015177045 A1 | 11/2015 |
| WO | 2015177046 A1 | 11/2015 |
| WO | 2015177252 A1 | 11/2015 |
| WO | 2015177253 A1 | 11/2015 |
| WO | 2015177254 A1 | 11/2015 |
| WO | 2015177255 A1 | 11/2015 |
| WO | 2015177256 A1 | 11/2015 |
| WO | 2015177257 A1 | 11/2015 |
| WO | 2015177263 A1 | 11/2015 |
| WO | 2015177264 A1 | 11/2015 |
| WO | 2015177265 A1 | 11/2015 |
| WO | 2015177294 A1 | 11/2015 |
| WO | 2016075436 A1 | 5/2016 |

OTHER PUBLICATIONS

"Digital controller for wireless battery charger (WBC) transmitters Qi 1.1.2 All certified, PMA compatible", STMicroelectronics NV, DocID027322, Feb. 2015, pp. 1-36.

* cited by examiner

```
                    ┌──────────────────────────────┐
          1500      │                              │
                    │                              │
         1502 ─┐    │ PROVIDE A SUBSTRATE COMPRISING AN │
                    │ AEROSOL PRECURSOR COMPOSITION │
                    └──────────────────────────────┘
                                │
                                ▼
         1504 ─┐    ┌──────────────────────────────┐
                    │ PROVIDE A RESONANT RECEIVER COUPLING │
                    │           DEVICE             │
                    └──────────────────────────────┘
                                │
                                ▼
         1506 ─┐    ┌──────────────────────────────┐
                    │ POSITION THE SUBSTRATE IN PROXIMITY TO │
                    │ THE RESONANT RECEIVER COUPLING DEVICE │
                    └──────────────────────────────┘
```

- 1502: PROVIDE A SUBSTRATE COMPRISING AN AEROSOL PRECURSOR COMPOSITION
- 1504: PROVIDE A RESONANT RECEIVER COUPLING DEVICE
- 1506: POSITION THE SUBSTRATE IN PROXIMITY TO THE RESONANT RECEIVER COUPLING DEVICE

1600

- 1602: PROVIDE A SUBSTRATE COMPRISING AN AEROSOL PRECURSOR COMPOSITION AND AN ATOMIZER
- 1604: PROVIDE A CONTROL BODY INCLUDING AN ELECTRICAL POWER SOURCE AND A WIRELESS POWER TRANSMITTER
- 1606: DIRECT CURRENT FROM ELECTRICAL POWER SOURCE TO THE WIRELESS POWER TRANSMITTER
- 1608: WIRELESSLY HEAT THE ATOMIZER WITH THE WIRELESS POWER TRANSMITTER TO HEAT THE AEROSOL PRECURSOR COMPOSITION TO PRODUCE AN AEROSOL

FIG. 16

INDUCTION-BASED AEROSOL DELIVERY DEVICE

TECHNOLOGICAL FIELD

The present disclosure relates to aerosol delivery devices such as smoking articles, and more particularly to aerosol delivery devices that may utilize electrically generated heat for the production of aerosol (e.g., smoking articles commonly referred to as electronic cigarettes). The smoking articles may be configured to heat an aerosol precursor, which may incorporate materials that may be made or derived from, or otherwise incorporate tobacco, the precursor being capable of forming an inhalable substance for human consumption.

BACKGROUND

Many devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous alternative smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 8,881,737 to Collett et al., U.S. Pat. App. Pub. No. 2013/0255702 to Griffith Jr. et al., U.S. Pat. App. Pub. No. 2014/0000638 to Sebastian et al., U.S. Pat. App. Pub. No. 2014/0096781 to Sears et al., U.S. Pat. App. Pub. No. 2014/0096782 to Ampolini et al., U.S. Pat. App. Pub. No. 2015/0059780 to Davis et al., and U.S. patent application Ser. No. 15/222,615 to Watson et al., filed Jul. 28, 2016, all of which are incorporated herein by reference. See also, for example, the various implementations of products and heating configurations described in the background sections of U.S. Pat. No. 5,388,594 to Counts et al. and U.S. Pat. No. 8,079,371 to Robinson et al., which are incorporated by reference.

Various implementations of aerosol delivery devices employ an atomizer to produce an aerosol from an aerosol precursor composition. Such atomizers often employ direct resistive heating to produce heat. In this regard, atomizers may include a heating element comprising a coil or other member that produces heat via the electrical resistance associated with the material through which an electrical current is directed. Electrical current is typically directed through the heating element via direct electrical connections such as wires or connectors. However, forming such electrical connections may complicate assembly of the aerosol delivery device and add potential points of failure. Further, in some implementations, the aerosol delivery device may include a control body, which may include a power source, and a cartridge, which may include the atomizer. In these implementations electrical connections between the cartridge and the control body may be required, which may further complicate the design of the aerosol delivery device. Thus, advances with respect to aerosol delivery devices may be desirable.

BRIEF SUMMARY

The present disclosure relates to aerosol delivery devices configured to produce aerosol and which aerosol delivery devices, in some implementations, may be referred to as electronic cigarettes or heat-not-burn cigarettes. As described hereinafter, the aerosol delivery devices may include a resonant transformer including a transmitter coupling device (sometimes referred to as an induction transmitter) and a resonant receiver coupling device (sometimes referred to as an induction receiver). The transmitter coupling device may include a coil configured to create an oscillating magnetic field (a magnetic field that varies periodically with time) when alternating current is directed therethrough. The resonant receiver coupling device may be at least partially received within the transmitter coupling device and may include a conductive material. Thereby, by directing alternating current through the transmitter coupling device, eddy currents may be generated in the resonant receiver coupling device via induction. The eddy currents flowing through the resistance of the material defining the resonant receiver coupling device may heat it by Joule heating. Thereby, the resonant receiver coupling device, which may define an atomizer, may be wirelessly heated to form an aerosol from an aerosol precursor composition positioned in proximity to the resonant receiver coupling device. Wireless heating, as used herein, refers to heating that occurs via an atomizer that is not physically electrically connected to the (electrical) power source. For further information, see U.S. patent application Ser. No. 14/934,763 to Davis et al., filed Nov. 6, 2015, and U.S. patent application Ser. No. 15/002,056 to Sur, filed Jan. 20, 2016, both of which are incorporated herein by reference.

The present disclosure includes, without limitation, the following example implementations.

Some example implementations provide an aerosol delivery device comprising a substrate configured to carry an aerosol precursor composition; a resonant transformer including a transmitter coupling device and a resonant receiver coupling device that is positioned in proximity to the substrate; and a pulse width modulation (PWM) inverter configured to drive the resonant transformer, the PWM inverter comprising: a bridge circuit coupled to the transmitter coupling device; and a PWM controller embodied as an integrated circuit and configured to output a PWM signal to the bridge circuit configured to drive the transmitter coupling device to generate an oscillating magnetic field and induce an alternating voltage in the resonant receiver coupling device when exposed to the oscillating magnetic field, the alternating voltage causing the resonant receiver coupling device to generate heat and thereby vaporize components of the aerosol precursor composition.

In some example implementations of the aerosol delivery device of the preceding or any subsequent example implementation, or any combination thereof, the aerosol delivery device further comprises a power source including a rechargeable supercapacitor, rechargeable solid-state battery or rechargeable lithium-ion battery, and configured to power the PWM inverter.

In some example implementations of the aerosol delivery device of any preceding or any subsequent example implementation, or any combination thereof, the aerosol delivery device further comprises a constant voltage regulator between the power source and PWM inverter, and configured to maintain a constant voltage level at the PWM inverter.

In some example implementations of the aerosol delivery device of any preceding or any subsequent example implementation, or any combination thereof, the aerosol delivery device further comprises a power source including a rechargeable supercapacitor, and configured to power the PWM inverter.

In some example implementations of the aerosol delivery device of any preceding or any subsequent example implementation, or any combination thereof, the power source further includes terminals connectable with a source of energy from which the rechargeable supercapacitor is chargeable.

In some example implementations of the aerosol delivery device of any preceding or any subsequent example implementation, or any combination thereof, the power source further comprises the source of energy, and the source of energy is or includes a rechargeable solid-state battery or rechargeable lithium-ion battery.

In some example implementations of the aerosol delivery device of any preceding or any subsequent example implementation, or any combination thereof, the bridge circuit is a half bridge composed of a pair of transistors and a pair of diodes.

In some example implementations of the aerosol delivery device of any preceding or any subsequent example implementation, or any combination thereof, the aerosol delivery device further comprises a Hall effect current sensor positioned proximate the resonant receiver coupling device and configured to produce a measurement of an alternating current induced therein; and a microprocessor configured to receive the measurement and control operation of at least one functional element of the aerosol delivery device in response thereto.

In some example implementations of the aerosol delivery device of any preceding or any subsequent example implementation, or any combination thereof, the aerosol delivery device further comprises a high-pass filter coupled to the resonant receiver coupling device, and configured to filter any direct voltage component from the alternating voltage induced in the resonant receiver coupling device; and a non-inverting amplifier circuit coupled to the high-pass filter, and configured to amplify the alternating voltage so filtered.

In some example implementations of the aerosol delivery device of any preceding or any subsequent example implementation, or any combination thereof, the transmitter coupling device is configured to at least partially surround the resonant receiver coupling device.

In some example implementations of the aerosol delivery device of any preceding or any subsequent example implementation, or any combination thereof, the transmitter coupling device defines a tubular or coiled configuration.

Some example implementations provide a control body coupled or coupleable with a cartridge that is equipped with a resonant receiver coupling device that is positioned in proximity to a substrate configured to carry an aerosol precursor composition, the control body comprising a transmitter coupling device that with the resonant receiver coupling device forms a resonant transformer when the control body is coupled with the cartridge; and a pulse width modulation (PWM) inverter configured to drive the resonant transformer, the PWM inverter comprising: a bridge circuit coupled to the transmitter coupling device; and a PWM controller embodied as an integrated circuit and configured to output a PWM signal to the bridge circuit configured to drive the transmitter coupling device to generate an oscillating magnetic field and induce an alternating voltage in the resonant receiver coupling device when exposed to the oscillating magnetic field, the alternating voltage causing the resonant receiver coupling device to generate heat and thereby vaporize components of the aerosol precursor composition.

In some example implementations of the control body of any preceding or any subsequent example implementation, or any combination thereof, the control body further comprises a power source including a rechargeable supercapacitor, rechargeable solid-state battery or rechargeable lithium-ion battery, and configured to power the PWM inverter.

In some example implementations of the control body of any preceding or any subsequent example implementation, or any combination thereof, the control body further comprises a constant voltage regulator between the power source and PWM inverter, and configured to maintain a constant voltage level at the PWM inverter.

In some example implementations of the control body of any preceding or any subsequent example implementation, or any combination thereof, the control body further comprises a power source including a rechargeable supercapacitor, and configured to power the PWM inverter.

In some example implementations of the control body of any preceding or any subsequent example implementation, or any combination thereof, the power source further includes terminals connectable with a source of energy from which the rechargeable supercapacitor is chargeable.

In some example implementations of the control body of any preceding or any subsequent example implementation, or any combination thereof, the power source further comprises the source of energy, and the source of energy is or includes a rechargeable solid-state battery or rechargeable lithium-ion battery.

In some example implementations of the control body of any preceding or any subsequent example implementation, or any combination thereof, the bridge circuit is a half bridge composed of a pair of transistors and a pair of diodes.

In some example implementations of the control body of any preceding or any subsequent example implementation, or any combination thereof, the transmitter coupling device is configured to at least partially surround the resonant receiver coupling device.

In some example implementations of the control body of any preceding or any subsequent example implementation, or any combination thereof, the transmitter coupling device defines a tubular or coiled configuration.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as intended, namely to be combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE DRAWING(S)

Having thus described the disclosure in the foregoing general terms, reference will now be made to the accompanying drawings, which are not necessarily drawn to scale, and wherein:

Figure 1:
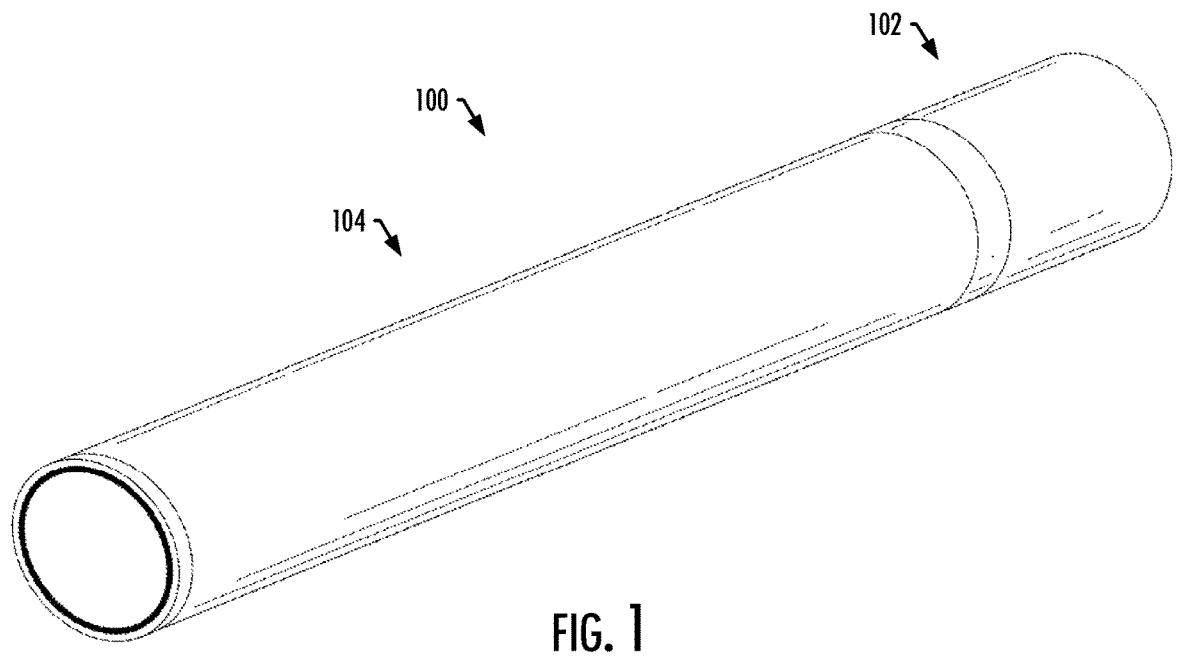
FIG. 1 illustrates a perspective view of an aerosol delivery device comprising a cartridge and a control body, wherein the cartridge and the control body are coupled to one another according to an example implementation of the present disclosure.

FIG. 15 schematically illustrates a method for assembling an aerosol delivery device according to an example implementation of the present disclosure; and FIG. 16 schematically illustrates a method for aerosolization according to an example implementation of the present disclosure.

DETAILED DESCRIPTION

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise. Also, while reference may be made herein to quantitative measures, values, geometric relationships or the like, unless otherwise stated, any one or more if not all of these may be absolute or approximate to account for acceptable variations that may occur, such as those due to engineering tolerances or the like.

As described hereinafter, example implementations of the present disclosure relate to aerosol delivery devices. Aerosol delivery devices according to the present disclosure use electrical energy to heat a material (preferably without combusting the material to any significant degree) to form an inhalable substance; and components of such systems have the form of articles most preferably are sufficiently compact to be considered hand-held devices. That is, use of components of preferred aerosol delivery devices does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery devices may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

While the systems are generally described herein in terms of implementations associated with aerosol delivery devices such as so-called "e-cigarettes," it should be understood that the mechanisms, components, features, and methods may be embodied in many different forms and associated with a variety of articles. For example, the description provided herein may be employed in conjunction with implementations of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of implementations relating to aerosol delivery devices by way of example only, and may be embodied and used in various other products and methods.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

Aerosol delivery devices of the present disclosure generally include a number of components provided within an outer body or shell, which may be referred to as a housing. The overall design of the outer body or shell can vary, and the format or configuration of the outer body that can define the overall size and shape of the aerosol delivery device can vary. Typically, an elongated body resembling the shape of a cigarette or cigar can be a formed from a single, unitary housing or the elongated housing can be formed of two or more separable bodies. For example, an aerosol delivery device can comprise an elongated shell or body that can be substantially tubular in shape and, as such, resemble the shape of a conventional cigarette or cigar. In one example, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., an accumulator such as a rechargeable battery and/or rechargeable supercapacitor, and various electronics for controlling the operation of that article), and at the other end and removably coupleable thereto, an outer body or shell containing a disposable portion (e.g., a disposable flavor-containing cartridge). More specific formats, configurations and arrangements of components within the single housing type of unit or within a multi-piece separable housing type of unit will be evident in light of the further disclosure provided herein. Additionally, various aerosol delivery device designs and component arrangements can be appreciated upon consideration of the commercially available electronic aerosol delivery devices.

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microprocessor, individually or as part of a microcontroller), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined airflow path through the article such that aerosol generated can be withdrawn therefrom upon draw).

Alignment of the components within the aerosol delivery device of the present disclosure can vary. In specific implementations, the aerosol precursor composition can be located near an end of the aerosol delivery device which may be configured to be positioned proximal to the mouth of a user so as to maximize aerosol delivery to the user. Other configurations, however, are not excluded. Generally, the heating element can be positioned sufficiently near the aerosol precursor composition so that heat from the heating element can volatilize the aerosol precursor (as well as one or more flavorants, medicaments, or the like that may likewise be provided for delivery to a user) and form an aerosol for delivery to the user. When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device may incorporate a battery or other electrical power source to provide current flow sufficient to provide various functionalities to the aerosol delivery device, such as powering of a heater, powering of control systems, powering of indicators, and the like. The power source can take on various implementations. Preferably, the power source is able to deliver sufficient power to rapidly heat the heating element to provide for aerosol formation and power the aerosol delivery device through use for a desired duration of time. The power source preferably is sized to fit conveniently within the aerosol delivery device so that the aerosol delivery device can be easily handled. Additionally, a preferred power source is of a sufficiently light weight to not detract from a desirable smoking experience.

More specific formats, configurations and arrangements of components within the aerosol delivery device of the present disclosure will be evident in light of the further disclosure provided hereinafter. Additionally, the selection of various aerosol delivery device components can be appreciated upon consideration of the commercially available electronic aerosol delivery devices. Further, the arrangement of the components within the aerosol delivery device can also be appreciated upon consideration of the commercially available electronic aerosol delivery devices.

As described hereinafter, the present disclosure relates to aerosol delivery devices. Aerosol delivery devices may be configured to heat an aerosol precursor composition to produce an aerosol. In some implementations, the aerosol delivery devices may comprise heat-not-burn devices, configured to heat a solid aerosol precursor composition (an extruded tobacco rod) or a semi-solid aerosol precursor composition (e.g., a glycerin-loaded tobacco paste). In another implementation, the aerosol delivery devices may be configured to heat and produce an aerosol from a fluid aerosol precursor composition (e.g., a liquid aerosol precursor composition). Such aerosol delivery devices may include so-called electronic cigarettes.

Regardless of the type of aerosol precursor composition heated, aerosol delivery devices may include a heating element configured to heat the aerosol precursor composition. In some implementations, the heating element may comprise a resistive heating element. Resistive heating elements may be configured to produce heat when an electrical current is directed therethrough. Such heating elements often comprise a metal material and are configured to produce heat as a result of the electrical resistance associated with passing an electrical current therethrough. Such resistive heating elements may be positioned in proximity to the aerosol precursor composition. For example, in some implementations, the resistive heating elements may comprise one or more coils of a wire wound about a liquid transport element (e.g., a wick, which may comprise a porous ceramic, carbon, cellulose acetate, polyethylene terephthalate, fiberglass, or porous sintered glass) configured to draw an aerosol precursor composition therethrough. Alternatively, the heating element may be positioned in contact with a solid or semi-solid aerosol precursor composition. Such configurations may heat the aerosol precursor composition to produce an aerosol.

In some implementations aerosol delivery devices may include a control body and a cartridge. The control body may be reusable, whereas the cartridge may be configured for a limited number of uses and/or configured to be disposable. The cartridge may include the aerosol precursor composition. In order to heat the aerosol precursor composition, the heating element may also be positioned in the cartridge. The control body may include a power source, which may be rechargeable or replaceable, and thereby the control body may be reused with multiple cartridges.

Although the above-described aerosol delivery devices may be employed to heat an aerosol precursor composition to produce aerosol, such configurations may suffer from one or more disadvantages. In this regard, resistive heating elements may comprise a wire defining one or more coils that contact the aerosol precursor composition. For example, as noted above, the coils may wrap around a liquid transport element (e.g., a wick) to heat and aerosolize an aerosol precursor composition directed to the heating element through the liquid transport element. However, as a result of the coils defining a relatively small surface area, some of the aerosol precursor composition may be heated to an unnecessarily high extent during aerosolization, thereby wasting energy. Alternatively or additionally, some of the aerosol precursor composition that is not in contact with the coils of the heating element may be heated to an insufficient extent for aerosolization. Accordingly, insufficient aerosolization may occur, or aerosolization may occur with wasted energy.

Further, as noted above, resistive heating elements produce heat when electrical current is directed therethrough. Accordingly, as a result of positioning the heating element in contact with the aerosol precursor composition, charring of the aerosol precursor composition may occur. Such charring may occur as a result of the heat produced by the heating element and/or as a result of electricity traveling through the aerosol precursor composition at the heating element. Charring may result in build-up of material on the heating element. Such material build-up may negatively affect the taste of the aerosol produced from the aerosol precursor composition.

As further described above, aerosol delivery devices may comprise a control body including a power source and a cartridge comprising a resistive heating element and an aerosol precursor composition. In order to direct electrical current to the resistive heating element, the control body and the cartridge may include electrical connectors configured to engage one another when the cartridge is engaged with the control body. However, usage of such electrical connectors may further complicate and increase the cost of such aerosol delivery devices. Additionally, in implementations of aerosol delivery devices including a fluid aerosol precursor composition, leakage thereof may occur at the terminals or other connectors within the cartridge.

Figure 2:
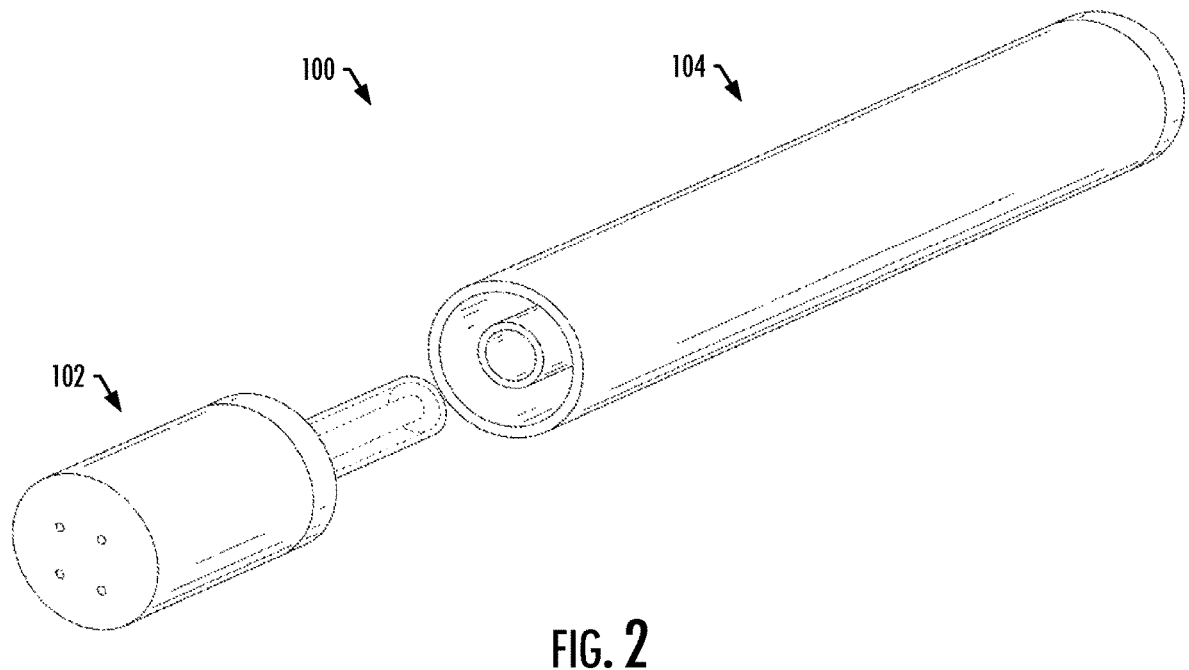
FIG. 2 illustrates a perspective view of the aerosol delivery device of FIG. 1 wherein the cartridge and the control body are decoupled from one another according to an example implementation of the present disclosure.

Thus, implementations of the present disclosure are directed to aerosol delivery devices which may avoid some or all of the problems noted above. In this regard, FIG. 1 illustrates an aerosol delivery device 100 according to an example implementation of the present disclosure. The aerosol delivery device may include a cartridge 102 and a control body 104. The cartridge and the control body can be permanently or detachably aligned in a functioning relationship. In this regard, FIG. 1 illustrates the aerosol delivery device in a coupled configuration, whereas FIG. 2 illustrates the aerosol delivery device in a decoupled configuration. Various mechanisms may connect the cartridge to the control body to result in a threaded engagement, a press-fit engagement, an interference fit, a magnetic engagement, or the like. The aerosol delivery device may be substantially rod-like, substantially tubular shaped, or substantially cylindrically shaped in some implementations when the cartridge and the control body are in an assembled configuration.

In specific implementations, one or both of the cartridge 102 and the control body 104 may be referred to as being disposable or as being reusable. For example, the control body may have a replaceable battery or a rechargeable battery, solid-state battery, thin-film solid-state battery, rechargeable supercapacitor or the like, and thus may be combined with any type of recharging technology, including connection to a wall charger, connection to a car charger (i.e., cigarette lighter receptacle), and connection to a computer, such as through a universal serial bus (USB) cable or connector (e.g., USB 2.0, 3.0, 3.1, USB Type-C), connection to a photovoltaic cell (sometimes referred to as a solar cell) or solar panel of solar cells, or wireless radio frequency (RF) based charger. Further, in some implementations, the cartridge 102 may comprise a single-use cartridge, as disclosed in U.S. Pat. No. 8,910,639 to Chang et al., which is incorporated herein by reference in its entirety.

Figure 3:
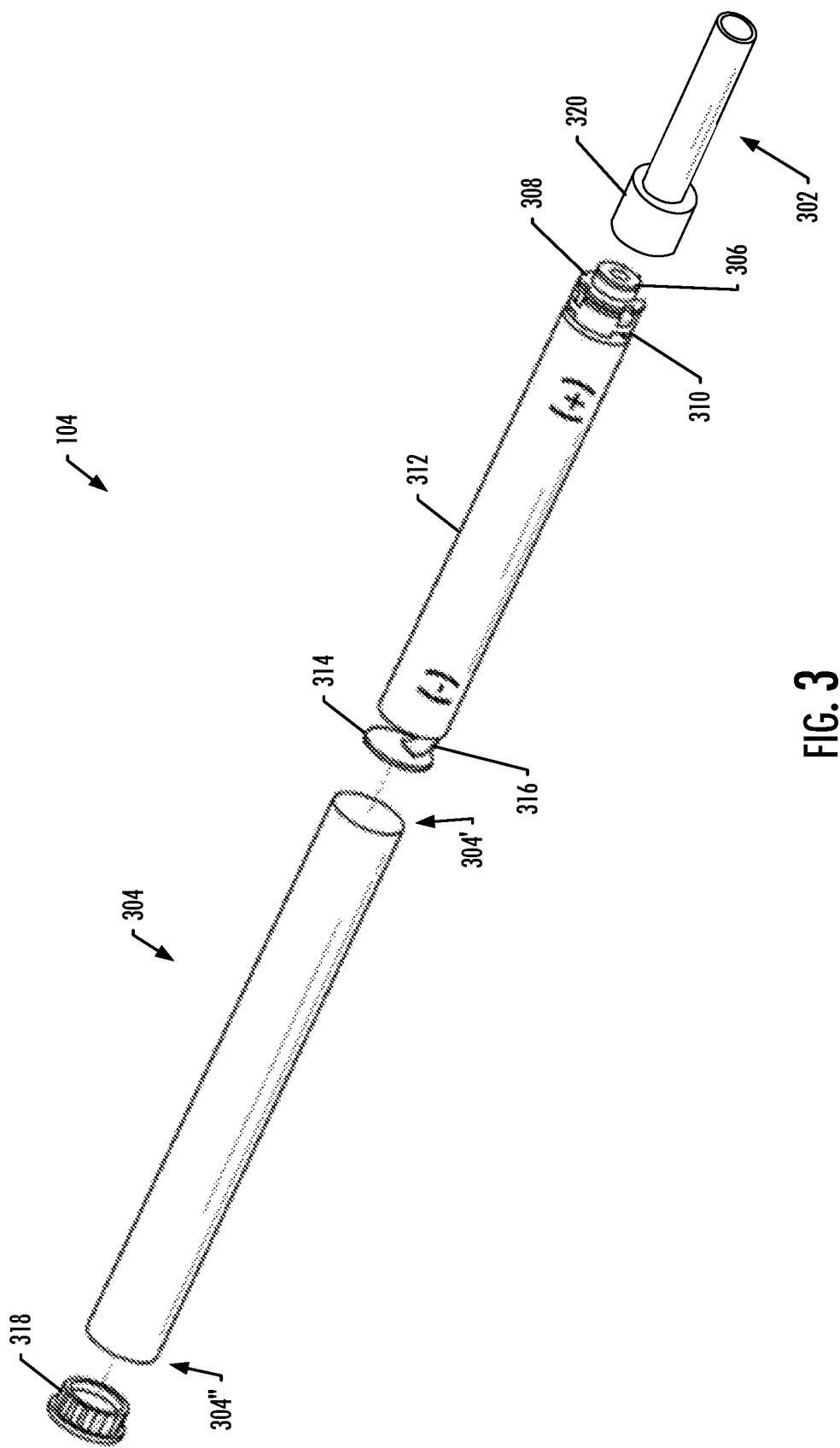
FIG. 3 illustrates an exploded view of the control body of FIG. 1 wherein an transmitter coupling device thereof defines a tubular configuration according to an example implementation of the present disclosure.

FIG. 3 illustrates an exploded view of the control body 104 of the aerosol delivery device 100 according to an example implementation of the present disclosure. As illustrated, the control body may comprise an transmitter coupling device 302, an outer body 304, a flow sensor 306 (e.g., a puff sensor or pressure switch), a control component 308 (e.g., a microprocessor, individually or as part of a microcontroller), a spacer 310, a power source 312 (e.g., a battery, which may be rechargeable, and/or a rechargeable supercapacitor), a circuit board with an indicator 314 (e.g., a light emitting diode (LED)), a connector circuit 316, and an end cap 318. Examples of power sources are described in U.S. Pat. No. 9,484,155 to Peckerar et al., and U.S. patent application Ser. No. 14/918,926 to Sur et al., filed Oct. 21, 2015, the disclosures of which are incorporated herein by reference in their respective entireties.

With respect to the flow sensor 306, representative current regulating components and other current controlling components including various microcontrollers, sensors, and switches for aerosol delivery devices are described in U.S. Pat. No. 4,735,217 to Gerth et al., U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference also is made to the control schemes described in U.S. Pat. No. 9,423,152 to Ampolini et al., which is incorporated herein by reference in its entirety.

In one implementation, the indicator 314 may comprise one or more light emitting diodes, quantum dot-based light emitting diodes or the like. The indicator can be in communication with the control component 308 through the connector circuit 316 and be illuminated, for example, during a user drawing on a cartridge (e.g., cartridge 102 of FIG. 2) coupled to the control body 104, as detected by the flow sensor 306. The end cap 318 may be adapted to make visible the illumination provided thereunder by the indicator. Accordingly, the indicator may be illuminated during use of the aerosol delivery device 100 to simulate the lit end of a smoking article. However, in other implementations, the indicator can be provided in varying numbers and can take on different shapes and can even be an opening in the outer body (such as for release of sound when such indicators are present).

Still further components can be utilized in the aerosol delivery device of the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and PCT Pat. App. Pub. No. WO 2010/003480 by Flick discloses a fluid flow sensing system indicative of a puff in an aerosol generating system; all of the foregoing disclosures being incorporated herein by reference in their entireties.

Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; PCT Pat. App. Pub. No. WO 2010/091593 to Hon; and PCT Pat. App. Pub. No. WO 2013/089551 to Foo, each of which is incorporated herein by reference in its entirety. Further, U.S. patent application Ser. No. 14/881,392 to Worm et al., filed Oct. 13, 2015, discloses capsules that may be included in aerosol delivery devices and fob-shape configurations for aerosol delivery devices, and is incorporated herein by reference in its entirety. A variety of the materials disclosed by the foregoing documents may be incorporated into the present devices in various implementations, and all of the foregoing disclosures are incorporated herein by reference in their entireties.

Each of the components of the control body 104 may be at least partially received in the outer body 304. The outer body may extend from an engagement end 304' to an outer end 304". The end cap 318 may be positioned at, and engaged with, the outer end of the outer body. Thereby, the end cap, which may be translucent or transparent, may be illuminated by the indicator 314 in order to simulate the lit end of a smoking article or perform other functions as described above. The opposing engagement end of the outer body may be configured to engage the cartridge 102.

Figure 4:
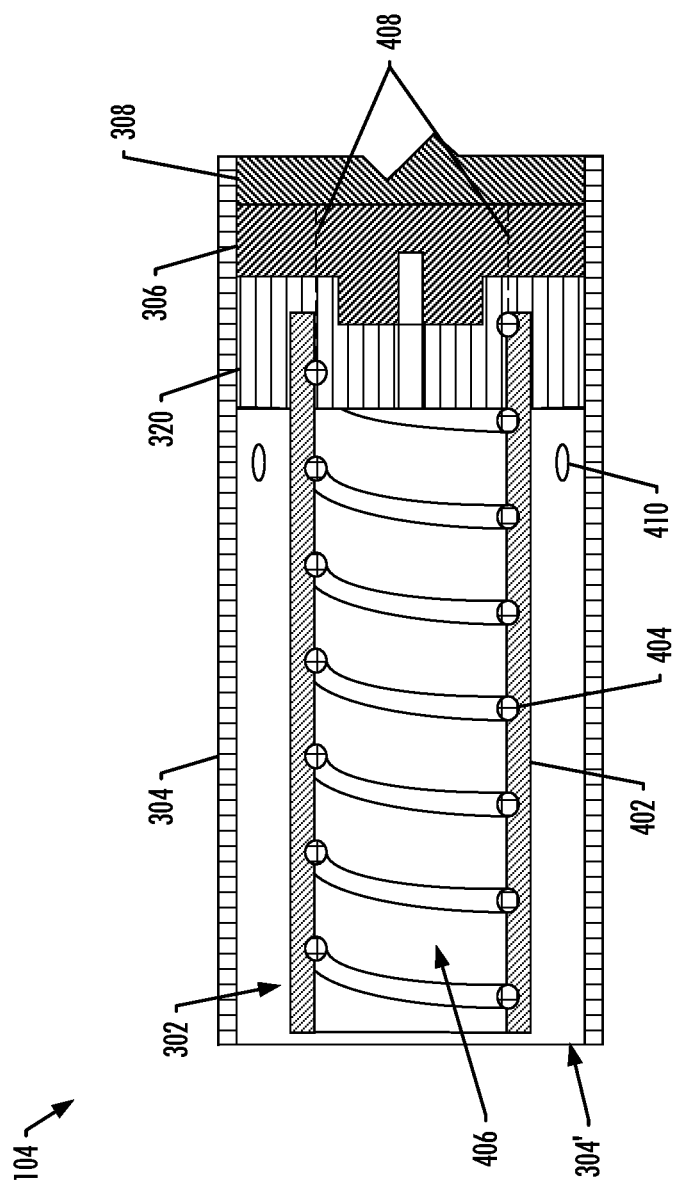
FIG. 4 illustrates a sectional view through the control body of FIG. 3.

FIG. 4 schematically illustrates a partial sectional view through the control body 104 proximate the engagement end 304' of the outer body 304. As illustrated, the transmitter coupling device 302 may extend proximate the engagement end of the outer body. In one implementation, as illustrated in FIGS. 3 and 4, the transmitter coupling device may define a tubular configuration. As illustrated in FIG. 4, the transmitter coupling device may include a coil support 402 and a coil 404. The coil support, which may define a tubular configuration, may be configured to support the coil such that the coil does not move into contact with, and thereby short-circuit with, the resonant receiver coupling device or other structures. The coil support may comprise a nonconductive material, which may be substantially transparent to the oscillating magnetic field produced by the coil. The coil may be imbedded in, or otherwise coupled to, the coil support. In the illustrated implementation, the coil is engaged with an inner surface of the coil support so as to reduce any losses associated with transmitting the oscillating magnetic field to the resonant receiver coupling device. However, in other implementations, the coil may be positioned at an outer surface of the coil support or fully imbedded in the coil support. Further, in some implementations, the coil may comprise an electrical trace printed on or otherwise coupled to the coil support, or a wire.

In either implementation, the coil may define a helical configuration.

Figure 5:
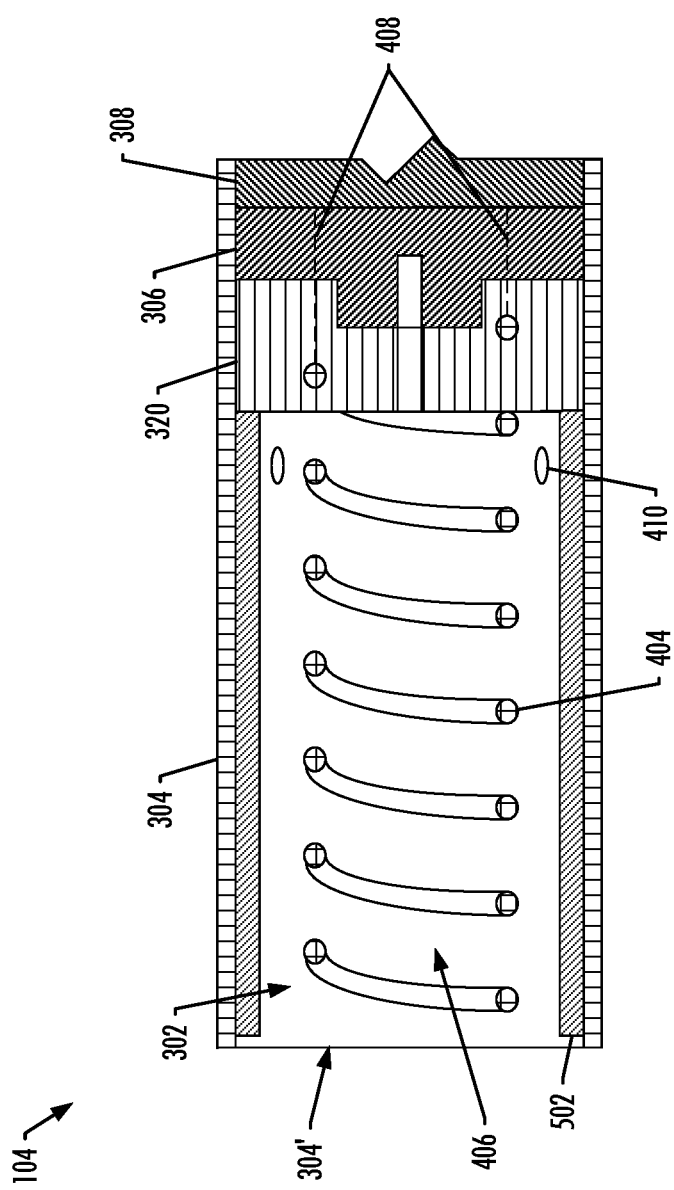
FIG. 5 illustrates a sectional view through the control body of FIG. 1 wherein an transmitter coupling device thereof defines a coiled configuration according to an example implementation of the present disclosure.

In an alternate implementation, as illustrated in FIG. 5, the transmitter coupling device 302 may include the coil 404 without the coil support 402. In each implementation, the transmitter coupling device may define an inner chamber 406 about which the transmitter coupling device extends.

As further illustrated in FIGS. 3-5, in some implementations, the transmitter coupling device 302 may be coupled to a support member 320. The support member may be configured to engage the transmitter coupling device and support the transmitter coupling device within the outer body 304. For example, the transmitter coupling device may be imbedded in, or otherwise coupled to the support member, such that the transmitter coupling device is fixedly positioned within the outer body. By way of further example, the transmitter coupling device may be injection molded into the support member.

The support member 320 may engage an internal surface of the outer body 304 to provide for alignment of the support member with respect to the outer body. Thereby, as a result of the fixed coupling between the support member and the transmitter coupling device 302, a longitudinal axis of the transmitter coupling device may extend substantially parallel to a longitudinal axis of the outer body. Thus, the transmitter coupling device may be positioned out of contact with the outer body, so as to avoid transmitting current from the transmitter coupling device to the outer body. However, in some implementations, as shown in FIG. 5, an optional insulator 502 may be positioned between the transmitter coupling device 302 and the outer body 304, so as to prevent contact therebetween. As may be understood, the insulator and the support member may comprise any nonconductive material such as an insulating polymer (e.g., plastic or cellulose), glass, rubber, and porcelain. Alternatively, the transmitter coupling device may contact the outer body in implementations in which the outer body is formed from a nonconductive material such as a plastic, glass, rubber, or porcelain.

As described below in detail, the transmitter coupling device 302 may be configured to receive an electrical current from the power source 312 and wirelessly heat the cartridge 102 (see, e.g., FIG. 2). Thus, as illustrated in FIGS. 4 and 5, the transmitter coupling device may include electrical connectors 408 configured to supply the electrical current thereto. For example, the electrical connectors may connect the transmitter coupling device to the control component. Thereby, current from the power source may be selectively directed to the transmitter coupling device as controlled by the control component. For example, the control component 312 may direct current from the power source (see, e.g., FIG. 3) to the transmitter coupling device when a draw on the aerosol delivery device 100 is detected by the flow sensor 306. The electrical connectors may comprise, by way of example, terminals, wires, or any other implementation of connector configured to transmit electrical current therethrough. Further, the electrical connectors may include a negative electrical connector and a positive electrical connector.

In some implementations, the power source 312 may comprise a battery and/or a rechargeable supercapacitor, which may supply direct current. As described elsewhere herein, operation of the aerosol delivery device may require directing alternating current to the transmitter coupling device 302 to produce an oscillating magnetic field in order to induce eddy currents in the resonant receiver coupling device. Accordingly, in some implementations, the control component 308 of the control body 104 may include an inverter or an inverter circuit configured to transform direct current provided by the power source to alternating current that is provided to the transmitter coupling device.

Figure 6:
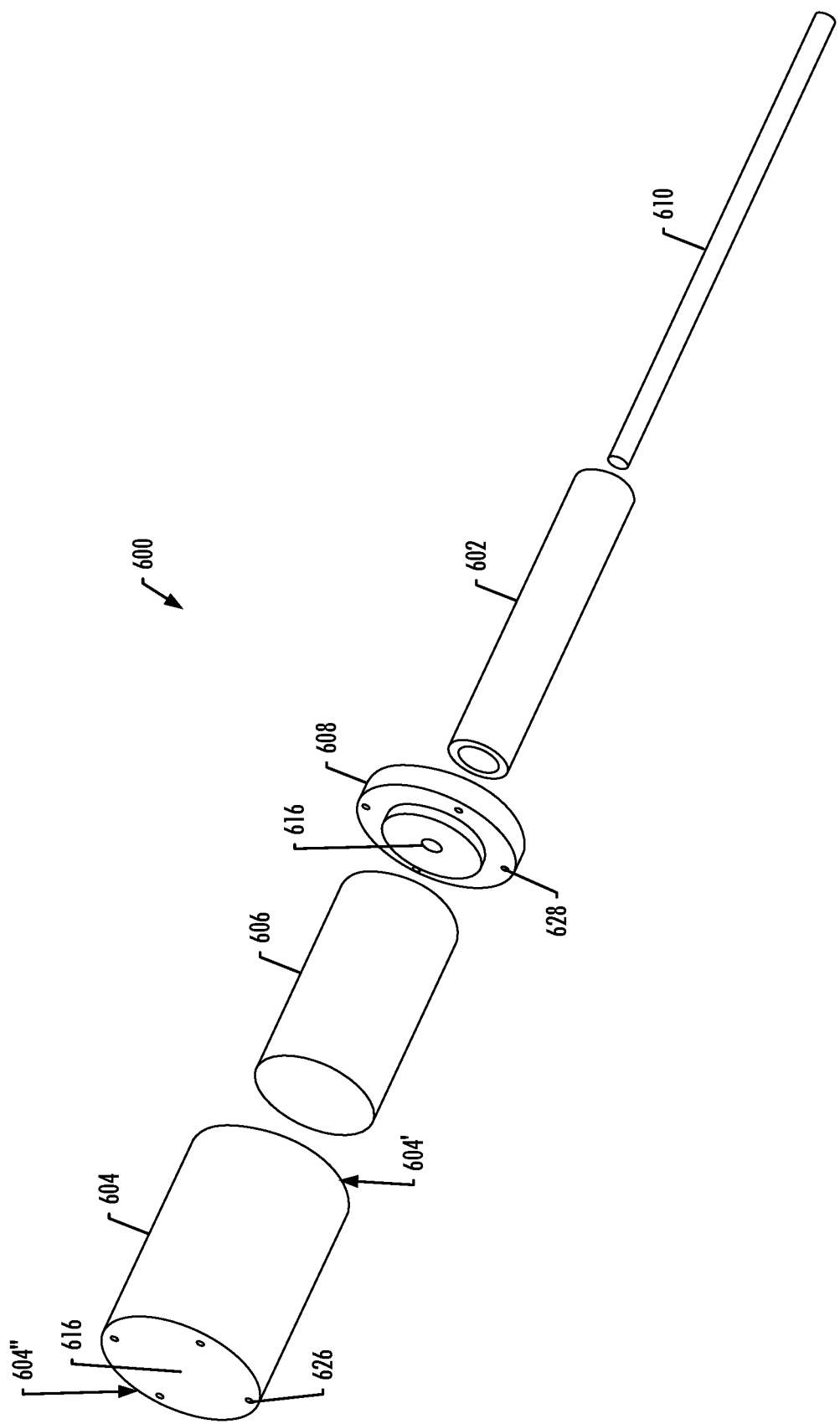
FIG. 6 illustrates an exploded view of the cartridge of FIG. 1 wherein a substrate thereof extends into an internal compartment defined by a container according to a first example implementation of the present disclosure.

FIG. 6 illustrates an exploded view of a cartridge 600 that in some examples may correspond to the cartridge 102 of FIG. 1. As illustrated, the cartridge 600 may include an resonant receiver coupling device 602, an outer body 604, a container 606, a sealing member 608, and a substrate 610. The outer body 604 may extend between an engagement end 604' and an outer end 604". Some or all of the remaining components of the cartridge 600 may be positioned at least partially within the outer body 604.

The cartridge 600 may additionally include a mouthpiece 612. The mouthpiece 612 may be integral with the outer body 604 or the container 606 or a separate component. The mouthpiece 612 may be positioned at the outer end 604" of the outer body 604.

Figure 7:
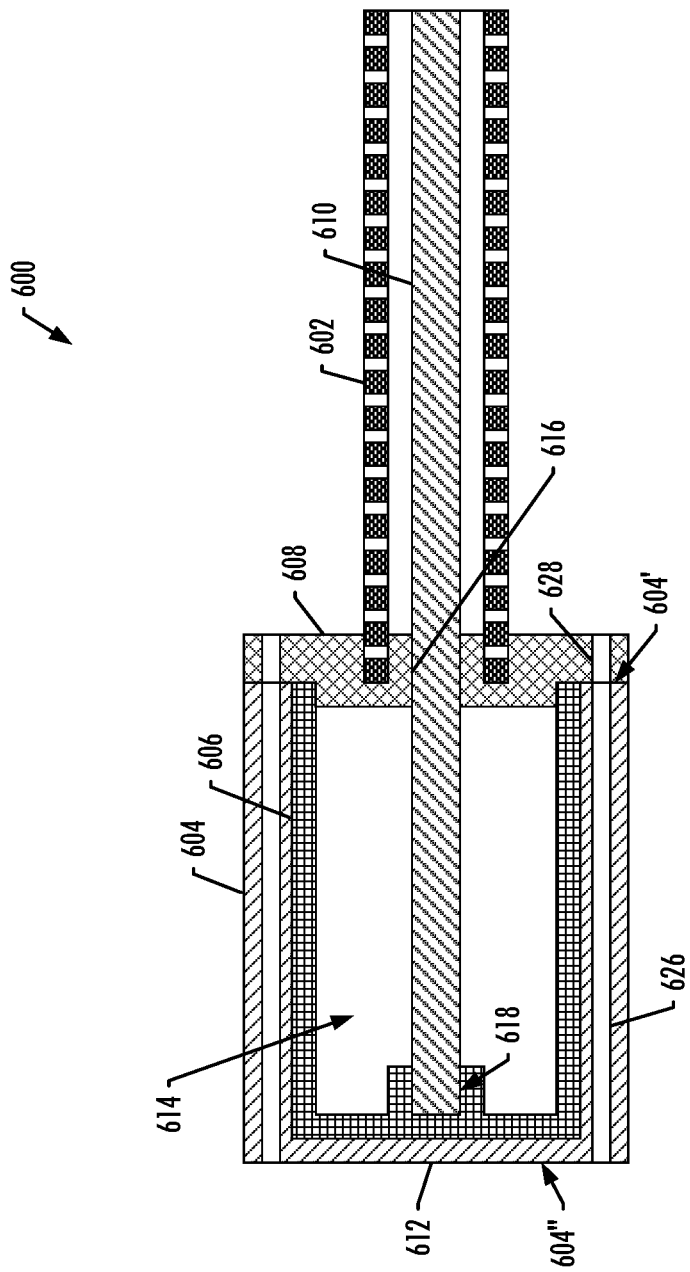
FIG. 7 illustrates a sectional view through the cartridge of FIG. 6.

FIG. 7 illustrates a sectional view through the cartridge 600 in an assembled configuration. As illustrated, the container 606 may be received within the outer body 604. Further the sealing member 608 may be engaged with the container 606 to define an internal compartment 614. As further illustrated in FIG. 7, in some implementations, the sealing member 608 may additionally engage the outer body 604.

In some implementations, the sealing member 608 may comprise an elastic material such as a rubber or silicone material. In these implementations, the sealing material 608 may compress to form a tight seal with the container 606 and/or the outer body 604. An adhesive may be employed to further improve the seal between the sealing member 608 and the container 606 and/or the outer body 604. In another implementation, the sealing member 608 may comprise an inelastic material such as a plastic material or a metal material. In these implementations, the sealing member 608 may be adhered or welded (e.g., via ultrasonic welding) to the container 606 and/or the outer body 604. Accordingly, via one or more of these mechanisms, the sealing member 608 may substantially seal the internal compartment 614 shut.

The resonant receiver coupling device 602 may be engaged with the sealing member 608. In one implementation, the resonant receiver coupling device 602 may be partially imbedded in the sealing member 608. For example, the resonant receiver coupling device 602 may be injection molded into the sealing member 608 such that a tight seal and connection is formed therebetween. Accordingly, the sealing member 608 may retain the resonant receiver coupling device at a desired position. For example, the resonant receiver coupling device 602 may be positioned such that a longitudinal axis of the resonant receiver coupling device extends substantially coaxially with a longitudinal axis of the outer body 604.

Further, the substrate 610 may engage the sealing member 608. In one implementation, the substrate 610 may extend through the sealing member 608. In this regard, the sealing member 608 may define an aperture 616 extending therethrough, and through which the substrate 610 is received. Thereby, the substrate 610 may extend into the internal compartment 614. For example, as illustrated in FIG. 7, an end of the substrate 610 may be received in a pocket 618 defined by the container 606. Accordingly, the container 606 and the sealing member 608 may each engage the substrate 610 and cooperatively maintain the substrate at a desired position. For example, a longitudinal axis of the substrate 610 may be positioned substantially coaxial with a longitudinal axis of the resonant receiver coupling device 602. Thereby, as illustrated, in some implementations, the substrate 610 may be positioned in proximity to, but out of contact with, the resonant receiver coupling device 602. By avoiding direct contact between the substrate 610 and the resonant receiver coupling device 602, the induction coil may remain substantially free of residue buildup from use, and hence the cartridge may optionally be refilled with aerosol precursor composition and/or a new substrate or otherwise reused. However, as discussed below, direct contact between the substrate and the resonant receiver coupling device may be preferable in some implementations.

The substrate 610 may include an aerosol precursor composition. The aerosol precursor composition may comprise one or more of a solid tobacco material, a semi-solid tobacco material, and a liquid aerosol precursor composition. For example, solid tobacco materials and semi-solid tobacco materials may be employed in implementations of the aerosol delivery device 100 defining so-called heat-not-burn cigarettes. Conversely, by way of further example, fluid (e.g., liquid) aerosol precursor compositions may be employed in implementations of the aerosol delivery device defining so-called electronic cigarettes.

Representative types of liquid aerosol precursor components and formulations are set forth and characterized in U.S. Pat. No. 7,726,320 to Robinson et al., U.S. Pat. No. 9,254,002 to Chong et al.; and U.S. Pat. App. Pub. Nos. 2013/0008457 to Zheng et al.; 2015/0020823 to Lipowicz et al.; and 2015/0020830 to Koller, as well as PCT Pat. App. Pub. No. WO 2014/182736 to Bowen et al.; and U.S. Pat. No. 8,881,737 to Collett et al., the disclosures of which are incorporated herein by reference. Other aerosol precursors that may be employed include the aerosol precursors that have been incorporated in the VUSE® product by R. J. Reynolds Vapor Company, the BLU product by Imperial Tobacco Group PLC, the MISTIC MENTHOL product by Mistic Ecigs, and the VYPE product by CN Creative Ltd. Also desirable are the so-called "smoke juices" for electronic cigarettes that have been available from Johnson Creek Enterprises LLC. Implementations of effervescent materials can be used with the aerosol precursor, and are described, by way of example, in U.S. Pat. App. Pub. No. 2012/0055494 to Hunt et al., which is incorporated herein by reference. Further, the use of effervescent materials is described, for example, in U.S. Pat. No. 4,639,368 to Niazi et al.; U.S. Pat. No. 5,178,878 to Wehling et al.; U.S. Pat. No. 5,223,264 to Wehling et al.; U.S. Pat. No. 6,974,590 to Pather et al.; U.S. Pat. No. 7,381,667 to Bergquist et al.; U.S. Pat. No. 8,424,541 to Crawford et al; U.S. Pat. No. 8,627,828 to Strickland et al.; and U.S. Pat. No. 9,307,787 to Sun et al., as well as US Pat. App. Pub. Nos. 2010/0018539 to Brinkley et al.; and PCT Pat. App. Pub. No. WO 97/06786 to Johnson et al., all of which are incorporated by reference herein.

Representative types of solid and semi-solid aerosol precursor compositions and formulations are disclosed in U.S. Pat. No. 8,424,538 to Thomas et al.; U.S. Pat. No. 8,464,726 to Sebastian et al.; U.S. Pat. App. Pub. No. 2015/0083150 to Conner et al.; U.S. Pat. App. Pub. No. 2015/0157052 to Ademe et al.; and U.S. patent application Ser. No. 14/755,205 to Nordskog et al., filed Jun. 30, 2015, all of which are incorporated by reference herein.

In implementations of the cartridge 102 wherein the aerosol precursor composition comprises a liquid or other fluid, the substrate 610 may be configured to retain the aerosol precursor composition therein and release a vapor therefrom when heat is applied thereto by the resonant receiver coupling device 602 in the manner described below. In some implementations, the substrate 610 may retain a sufficient quantity of the aerosol precursor composition to last a desired extent. In other implementations it may be preferable to provide the cartridge 102 with an increased capacity of the aerosol precursor composition. Examples of materials that may be employed in the substrate 610 in implementations wherein the substrate is configured to hold a fluid aerosol precursor composition include a porous ceramic, carbon, cellulose acetate, polyethylene terephthalate, fiberglass, and porous sintered glass.

In this regard, as illustrated by way of example in FIGS. 6 and 7, in one implementation, the container 606 may comprise a reservoir and the internal compartment 614 may be configured to receive the liquid aerosol precursor composition. In this implementation, the substrate 610 may comprise a liquid transport element (e.g., a wick) configured to receive the aerosol precursor composition from the internal compartment 614 and transport the aerosol precursor composition therealong. Accordingly, the aerosol precursor composition may be transported from the internal compartment 614 to locations along the longitudinal length of the substrate 610 about which the resonant receiver coupling device 602 extends.

As may be understood, the implementation of the cartridge 600 illustrated in FIG. 7 is provided for example purposes only. In this regard, various alternative implementations of cartridges 102 are provided herein by way of further example. Note that although the implementations of the cartridge 102 are described separately herein, each of the respective components and features thereof may be combined in any manner except as may be otherwise noted herein.

Figure 8:
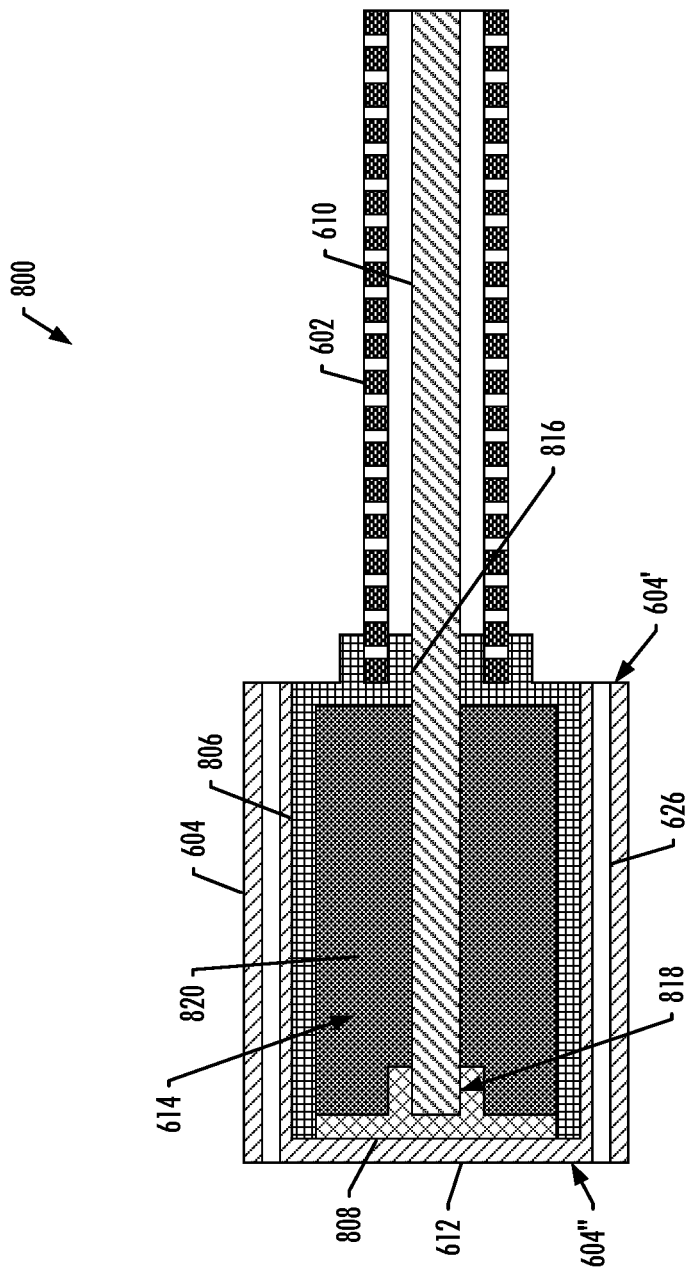
FIG. 8 illustrates a sectional view through the cartridge of FIG. 1 including a reservoir substrate in an internal compartment defined by a container according to a second example implementation of the present disclosure.

FIG. 8 illustrates another cartridge 800 that in some examples may correspond to the cartridge 102 of FIG. 1. The cartridge 800 is similar to cartridge 700, but in which the sealing member 708 is positioned proximate the outer end 604" of the outer body 604, as opposed to at the engagement end 604'. In this implementation, the container 806 may include the aperture 816 extending therethrough and the sealing member 808 may define the pocket 818, in order to support the substrate 610 in substantially the same manner as described above. Accordingly, the sealing member 608 may be positioned at the engagement end 604' of the container 606, (see FIG. 7), or the sealing member 808 may be positioned at the outer end 604" of the container 806 (see FIG. 8).

In some implementations, the container may be sufficiently sealed such that leakage of the aerosol precursor composition is substantially avoided. However, as illustrated in FIG. 8, in some implementations, the cartridge 800 may further comprise a reservoir substrate 820. As may be understood, the reservoir substrate 820 may be employed in any of the cartridges disclosed herein including an internal compartment 614.

In one implementation, the reservoir substrate 820 may comprise a plurality of layers of nonwoven fibers formed into substantially the shape of a tube fully or partially encircling the substrate 610 within the internal compartment 820. In other implementations, the reservoir substrate 820 may comprise a porous ceramic, carbon, cellulose acetate, polyethylene terephthalate, fiberglass, or porous sintered glass. Thereby, a liquid aerosol precursor composition can be sorptively retained by the reservoir substrate 820. As a result of contact between the reservoir substrate 820 and the reservoir, the reservoir substrate is in fluid communication with the substrate 610. Thus, the substrate 610 may be configured to transport the liquid aerosol precursor composition from the reservoir substrate 820 in the internal compartment 614 via capillary action or other liquid transport mechanisms to locations along the longitudinal length of the substrate 610 outside of the internal compartment.

Figure 9:
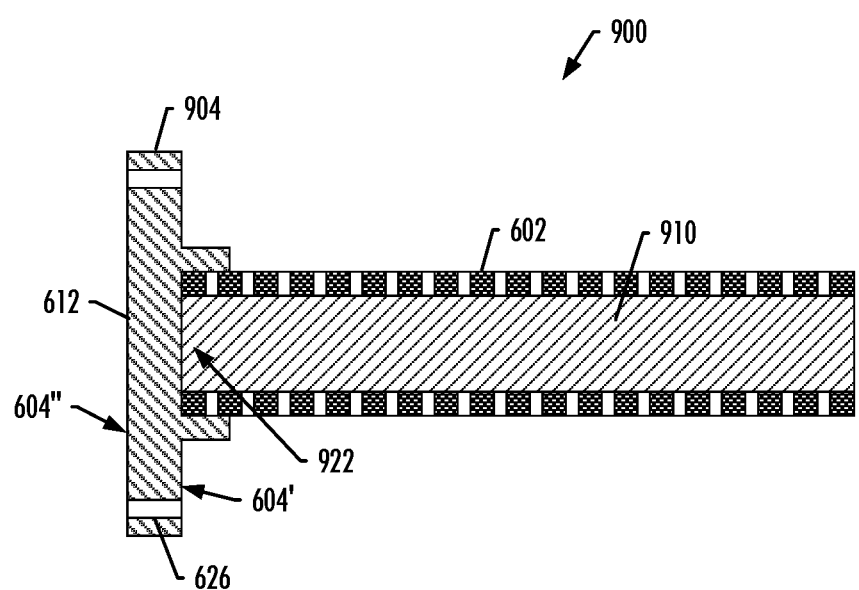
FIG. 9 illustrates a sectional view through the cartridge of FIG. 1 including a substrate in contact with an resonant receiver coupling device according to a third example implementation of the present disclosure.

As noted above, in some implementations of the cartridge 600, 800, the substrate 610 may be positioned in proximity to, but out of contact with, the resonant receiver coupling device 602. Such a configuration may avoid build-up of residue on the resonant receiver coupling device due to the lack of direct contact therebetween. However, in other implementations, the substrate 610 may contact the resonant receiver coupling device. In this regard, FIG. 9 illustrates yet another cartridge 900 that in some examples may correspond to the cartridge 102 of FIG. 1, similar to cartridges 600, 800 but in which the substrate 910 may contact the resonant receiver coupling device 602. Usage of this configuration may allow for a relatively larger substrate 910, which may contain a relatively greater quantity of the aerosol precursor composition, without necessarily increasing the size of the resonant receiver coupling device 602. Further, direct contact between the resonant receiver coupling device and the substrate may facilitate heat transfer from the resonant receiver coupling device to the substrate via convection, which may be significantly more efficient than the radiant heating employed in implementations in which there is no direct contact therebetween. Accordingly, it should be understood that each of the implementations of the cartridges disclosed herein may include direct contact between the resonant receiver coupling device and the substrate and/or the aerosol precursor composition. Providing for direct contact between the substrate 910 and the resonant receiver coupling device 602 may be employed, by way of example, in implementations in which aerosol precursor composition comprises a solid tobacco material or a semi-solid tobacco material, which may be less prone to causing residue build-up on the resonant receiver coupling device than a liquid aerosol precursor composition.

In the implementations of the cartridges 600, 800 illustrated in FIGS. 6-8, the substrate 610 extends into the internal compartment 614. However, in other implementations, the cartridge may not define an internal compartment. For example, the cartridge 900 illustrated in FIG. 9 does not include an internal compartment. In this regard, the substrate 910 may comprise a sufficient quantity of the aerosol precursor composition, such that usage of an internal compartment may not be need in some implementations. Thus, for example, the resonant receiver coupling device 602 and the substrate 910 may be substantially coextensive, such that the longitudinal ends thereof terminate at substantially the same points. In this regard, the substrate resonant receiver coupling device 602 and/or the substrate 910 may be received in a pocket 922 defined by the outer body 904 or otherwise engaged (e.g., directly engaged) with the outer body. Thus, in some implementations, the cartridge 900 may define a relatively simple configuration that may not include a container, a sealing member, or an internal compartment. Such a configuration may reduce the complexity and/or cost of the cartridge 900.

Figure 10:
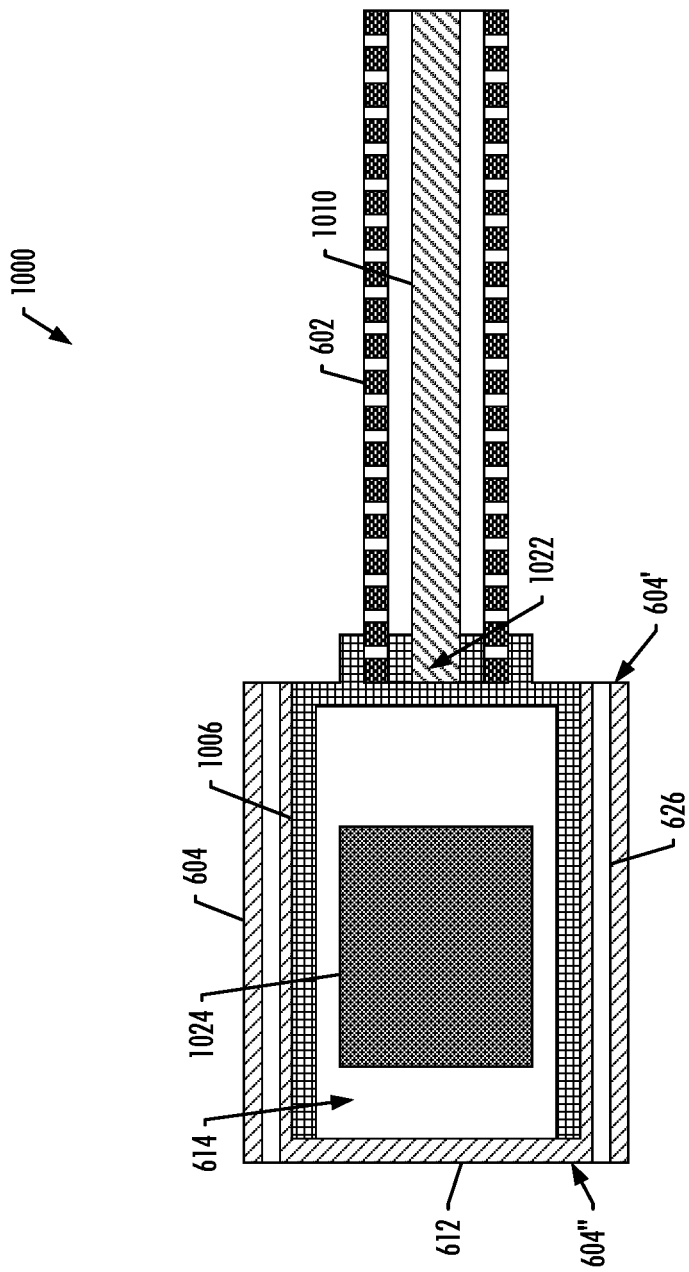
FIG. 10 illustrates a sectional view through the cartridge of FIG. 1 including an electronic control component according to a fourth example implementation of the present disclosure.

As described above, in some implementations, the substrate 910 may not extend into an internal compartment and may instead terminate, for example, proximate the outer body 904. As further described above with respect to FIG. 9, in one implementation, the cartridge 900 may not include a container or an internal compartment. However, in another implementation, the cartridge may include the container defining the internal compartment without the substrate extending into the compartment. This is shown in FIG. 10, which illustrates yet another cartridge 1000 that may correspond to the cartridge 104 of FIG. 1. As shown, the cartridge 1000 may include the container 1006 defining the internal compartment 614 without the substrate 1010 extending into the compartment. In this regard, the resonant receiver coupling device 602 and the substrate 1010 may be engaged with the container or the outer body. For example, in FIG. 10, the resonant receiver coupling device 602 and the substrate 1010 are each engaged with the container 1006. By way of further example, as described above, the resonant receiver coupling device 602 may be partially embedded in the container 1006. Further, the substrate 1010 may engage a pocket 1022 defined by the container 1006.

By configuring the cartridge 1000 such that the substrate 1010 does not extend into the internal compartment 614, the compartment may be employed for purposes other than a reservoir for the aerosol precursor composition. For example, as illustrated in FIG. 10, in some implementations, the cartridge 1000 may include an electronic control component 1024. As described below, the electronic control component 1024 may be employed in authentication of the cartridge 1000 or employed for other purposes.

Figure 11:
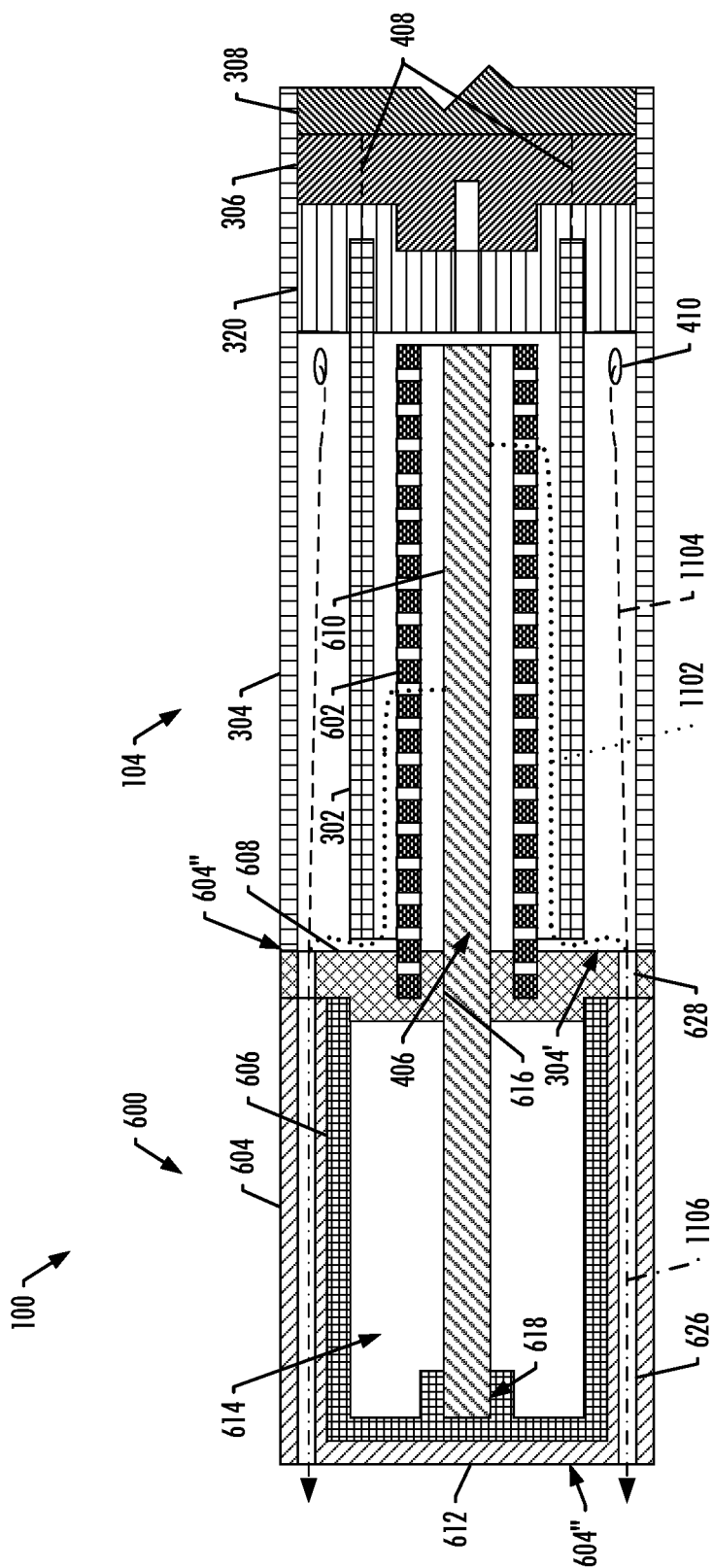
FIG. 11 illustrates a sectional view through the aerosol delivery device of FIG. 1 including the cartridge of FIG. 6 and the control body of FIG. 3 according to an example implementation of the present disclosure.

As noted above, each of the cartridges 102 of the present disclosure is configured to operate in conjunction with the control body 104 to produce an aerosol. By way of example, FIG. 11 illustrates the cartridge 600 engaged with the control body 104. As illustrated, when the control body 104 is engaged with the cartridge 600, the transmitter coupling device 302 may at least partially surround, preferably substantially surround, and more preferably fully surround the resonant receiver coupling device 602 (e.g., by extending around the circumference thereof). Further, the transmitter coupling device 302 may extend along at least a portion of the longitudinal length of the resonant receiver coupling device 602, and preferably extend along a majority of the longitudinal length of the resonant receiver coupling device, and most preferably extend along substantially all of the longitudinal length of the resonant receiver coupling device.

Accordingly, the resonant receiver coupling device 602 may be positioned inside of the inner chamber 406 about which the transmitter coupling device 302 extends. Accordingly, when a user draws on the mouthpiece 612 of the cartridge 600, the pressure sensor 306 may detect the draw. Thereby, the control component 308 may direct current from the power source 312 (see, e.g., FIG. 3) to the transmitter coupling device 302. The transmitter coupling device 302 may thereby produce an oscillating magnetic field. As a result of the resonant receiver coupling device 602 being received in the inner chamber 406, the resonant receiver coupling device may be exposed to the oscillating magnetic field produced by the transmitter coupling device 302.

In particular, the transmitter coupling device 302 and the resonant receiver coupling device 602 may form an electrical transformer. In some examples, the resonant transformer and associated circuitry including the PWM inverter may be configured to operate according to a suitable wireless power transfer standard such as the Qi interface standard developed by the Wireless Power Consortium (WPC), the Power Matters Alliance (PMA) interface standard developed by the PMA, the Rezence interface standard developed by the Alliance for Wireless Power (A4WP), and the like.

According to example implementations, a change in current in the transmitter coupling device 302, as directed thereto from the power source 312 (see, e.g., FIG. 3) by the control component 308, may produce an alternating electromagnetic field that penetrates the resonant receiver coupling device 602, thereby generating electrical eddy currents within the resonant receiver coupling device. The alternating electromagnetic field may be produced by directing alternating current to the transmitter coupling device 302. As noted above, in some implementations, the control component 308 may include an inverter or inverter circuit configured to transform direct current provided by the power source 312 to alternating current that is provided to the transmitter coupling device 302.

The eddy currents flowing the material defining the resonant receiver coupling device 602 may heat the resonant receiver coupling device through the Joule effect, wherein the amount of heat produced is proportional to the square of the electrical current times the electrical resistance of the material of the resonant receiver coupling device. In implementations of the resonant receiver coupling device 602 comprising magnetic materials, heat may also be generated by magnetic hysteresis losses. Several factors contribute to the temperature rise of the resonant receiver coupling device 602 including, but not limited to, proximity to the transmitter coupling device 302, distribution of the magnetic field, electrical resistivity of the material of the resonant receiver coupling device, saturation flux density, skin effects or depth, hysteresis losses, magnetic susceptibility, magnetic permeability, and dipole moment of the material.

In this regard, both the resonant receiver coupling device 602 and the transmitter coupling device 302 may comprise an electrically conductive material. By way of example, the transmitter coupling device 302 and/or the resonant receiver coupling device 602 may comprise various conductive materials including metals such as cooper and aluminum, alloys of conductive materials (e.g., diamagnetic, paramagnetic, or ferromagnetic materials) or other materials such as a ceramic or glass with one or more conductive materials imbedded therein. In another implementation, the resonant receiver coupling device may comprise conductive particles or objects of any of various sizes received in a reservoir filled with the aerosol precursor composition. In some implementations, the resonant receiver coupling device may be coated with or otherwise include a thermally conductive passivation layer (e.g., a thin layer of glass), to prevent direct contact with the aerosol precursor composition.

Accordingly, the resonant receiver coupling device 602 may be heated. The heat produced by the resonant receiver coupling device 602 may heat the substrate 610 including the aerosol precursor composition, such that an aerosol 1102 is produced. Accordingly, the resonant receiver coupling device 602 may comprise an atomizer. By positioning the resonant receiver coupling device 602 around the substrate 610 at a substantially uniform distance therefrom (e.g., by aligning the longitudinal axes of the substrate and the resonant receiver coupling device), the substrate and the aerosol precursor composition may be substantially uniformly heated.

The aerosol 1102 may travel around or through the resonant receiver coupling device 602 and the transmitter coupling device 302. For example, as illustrated, in one implementation, the resonant receiver coupling device 602 may comprise a mesh, a screen, a helix, a braid, or other porous structure defining a plurality of apertures extending therethrough. In other implementations, the resonant receiver coupling device may comprise a rod imbedded in a substrate or otherwise in contact with an aerosol precursor composition, a plurality of beads or particles imbedded in a substrate or otherwise in contact with an aerosol precursor composition, or a sintered structure. In each of these implementations, the aerosol 1102 may freely pass through the resonant receiver coupling device 602 and/or the substrate to allow the aerosol to travel through the mouthpiece to the user.

The aerosol 1102 may mix with air 1104 entering through inlets 410 (see, e.g., FIG. 4), which may be defined in the control body 104 (e.g., in the outer body 304). Accordingly, an intermixed air and aerosol 1106 may be directed to the user. For example, the intermixed air and aerosol 1106 may be directed to the user through one or more through holes 626 defined in the outer body 604 of the cartridge 600. In some implementations, the sealing member 608 may additionally include through holes 628 extending therethrough, which may align with the through holes 626 defined through the outer body 604. However, as may be understood, the flow pattern through the aerosol delivery device 100 may vary from the particular configuration described above in any of various manners without departing from the scope of the present disclosure.

As further noted above, in some implementations, the cartridge 102 may further comprise a second electronic control component. For example, the cartridge 1000 illustrated in FIG. 10 includes second control component 1024. The second control component 1024 may be configured to allow for authentication of the cartridge 1000. In this regard, in some implementations, the second control component 1024 may be configured to output a code to the control body 104 which the (first) control component 308 (see, e.g., FIG. 3) can analyze. Thereby, for example, the control component 308 may direct current to the transmitter coupling device 302 only when the cartridge 1000 is verified as authentic. In some implementations, the second control component may include terminals that connect to the control body. More preferably, the second control component 1024 may comprise a radio-frequency identification (RFID) chip configured to wirelessly transmit a code or other information to the control body 104. Thereby, the aerosol delivery device 100 may be used without requiring engagement of electrical connectors between the cartridge and the control body. Further, various examples of control components and functions performed thereby are described in U.S. Pat. App. Pub. No. 2014/0096782 to Sears et al., which is incorporated herein by reference in its entirety.

Figure 12:
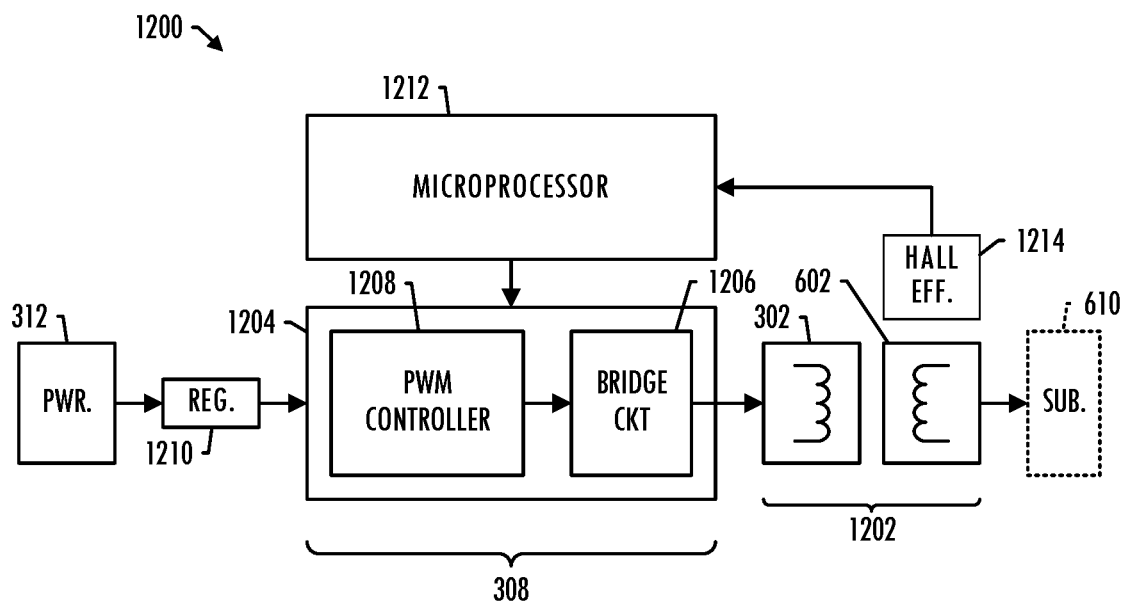
FIGS. 12, 13 and 14 illustrate circuitry and other components of the aerosol delivery device according to example implementations.
Figure 13:
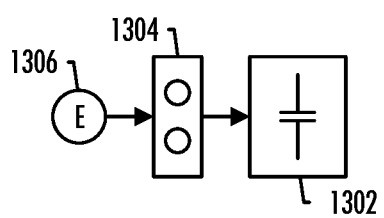
Figure 14:
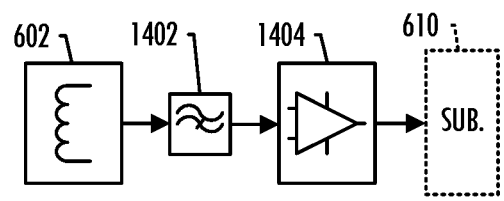

As indicated above, in some implementations, the control component 308 of the control body 104 may include an inverter or an inverter circuit configured to transform direct current provided by the power source 312 to alternating current that is provided to the transmitter coupling device 302. FIGS. 12, 13 and 14 illustrate circuitry 1200 and other components of the aerosol delivery device 100 according to example implementations of the present disclosure. As shown, the aerosol delivery device includes a substrate 610 configured to carry an aerosol precursor composition, and circuitry including a resonant transformer 1202 including a transmitter coupling device 302 and a resonant receiver coupling device 602 that is positioned in proximity to the substrate. And the control component 308 of the aerosol delivery device includes a pulse width modulation (PWM) inverter 1204 configured to drive the resonant transformer.

As shown, the PWM inverter 1204 includes a bridge circuit 1206 coupled to the transmitter coupling device 302, and which in some examples is a half bridge composed of a pair of transistors such as metal-oxide-semiconductor field-effect transistors (MOSFETs), and a pair of diodes. The PWM inverter also includes a PWM controller 1208 coupled to the bridge circuit. According to some examples, the PWM controller is embodied as an integrated circuit and configured to output a PWM signal to the bridge circuit configured to drive the transmitter coupling device to generate an oscillating magnetic field and induce an alternating voltage in the resonant receiver coupling device 602 when exposed to the oscillating magnetic field. This alternating voltage causes the resonant receiver coupling device to generate heat and thereby vaporize components of the aerosol precursor composition. Examples of suitable PWM controllers include the bq500210 and bq500212A controllers from Texas Instruments, the STWBC series controllers from STMicroelectronics, and the like.

As also shown, in some examples, the aerosol delivery device 100 further includes a power source 312, such as a rechargeable supercapacitor, rechargeable solid-state battery or rechargeable lithium-ion battery, configured to power the PWM inverter 1204. In some further examples, the aerosol delivery device further includes a constant voltage regulator 1210 between the power source and PWM inverter, and configured to maintain a constant voltage level at the PWM inverter. Examples of suitable voltage regulators include switching regulators, linear regulars such as low-dropout (LDO) regulators, and the like.

FIG. 13 illustrates a power source 1300 that may correspond to the power source 312 in some examples. As shown, in some examples, the power source includes a rechargeable supercapacitor 1302 configured to power the PWM inverter 1204. In some further examples, the power source further includes terminals 1304 connectable with a source of energy 1306 from which the rechargeable supercapacitor is chargeable. As indicated above, for example, the control body 104 may be combined with any type of recharging technology (e.g., wall charger, car charger, computer, photovoltaic cell, solar panel of solar cells, wireless RF based charger). And in yet further examples, the power source further includes the source of energy, and the source of energy is or includes a rechargeable solid-state battery or rechargeable lithium-ion battery.

Returning to FIG. 12, in some examples, the aerosol delivery device 100 may further protect against the temperature of the resonant receiver coupling device 602 reaching or exceeding a threshold temperature. In some of these examples, the control component 308 includes a microprocessor 1212 configured to receive a measurement of an alternating current induced in the resonant receiver coupling device 602, such as from a Hall effect current sensor 1214 positioned proximate the resonant receiver coupling device 602. This Hall effect current sensor may be part of the cartridge 102, or in some examples, the control body 104. The microprocessor may then control operation of at least one functional element of the aerosol delivery device in response to the measurement, such as to reduce the temperature of the resonant receiver coupling device 602 in instances in which the measurement indicates a temperature at or above a threshold temperature. One manner of reducing temperature may be to include further air outlets in the aerosol delivery device, may be control to vent air out of the aerosol delivery device 100. Some examples of a suitable aerosol delivery device equipped with a Hall effect current sensor are described in U.S. patent application Ser. No. 14/993,762 to Sur, filed Jan. 12, 2016, which is incorporated herein by reference in its entirety.

As shown in FIG. 14, in some examples, the aerosol delivery device further includes a high-pass filter 1402, and a non-inverting amplifier circuit 1404 coupled to the high-pass filter. In these examples, the high-pass filter is coupled to the resonant receiver coupling device 602, and configured to filter any direct voltage component from the alternating voltage induced in the resonant receiver coupling device. The non-inverting amplifier circuit, then, is configured to amplify the alternating voltage so filtered.

As described above, the present disclosure relates to aerosol delivery device including a control body comprising a wireless power transmitter configured to receive an electrical current from a power source and wirelessly heat an atomizer. As may be understood, various wireless heating techniques may be employed to heat an aerosol precursor composition, which may be contained in a reservoir and/or in contact with a substrate. In some implementations, the atomizer may be wirelessly heated without transmitting electrical current to the atomizer.

In the implementations described above, the wireless power transmitter may comprise an transmitter coupling device, and the atomizer may comprise an resonant receiver coupling device. Thereby, eddy currents may be induced at the resonant receiver coupling device in order to produce heat. As further noted above, the transmitter coupling device may be configured to at least partially surround the resonant receiver coupling device. By way of further example, in other implementations, the atomizer may be wirelessly heated using radiant heating, sonic heating, photonic heating (e.g., via a laser), and/or microwave heating.

However, various other techniques and mechanisms may be employed in other implementations to wirelessly heat an atomizer. For example, electrical current may be wirelessly transmitted to an atomizer, and such wireless power transmission techniques may be employed with any implementation of atomizer such as wire coil resistive heating elements. Example implementations of wireless power transmission methods and mechanisms are provided in U.S. patent application Ser. No. 14/814,866 to Sebastian et al., filed Jul. 31, 2015, which is incorporated herein by reference in its entirety.

Note that although the present disclosure generally describes heating a substrate comprising an aerosol precursor composition positioned in proximity to the resonant receiver coupling device to produce an aerosol, in other implementations, the resonant receiver coupling device may be configured to heat an aerosol precursor composition directed (e.g., dispensed) thereto. For example, U.S. Pat. App. Pub. Nos. 2015/0117842; 2015/0114409; and 2015/0117841, each to Brammer et al., disclose fluid aerosol precursor composition delivery mechanisms and methods, which are incorporated herein by reference in their entireties. Such fluid aerosol precursor composition delivery mechanisms and methods may be employed to direct an aerosol precursor composition from a reservoir to the resonant receiver coupling device to produce an aerosol. In an additional implementation, the resonant receiver coupling device may comprise a hollow needle connected to a reservoir, wherein capillary action directs the aerosol precursor composition into the needle to replenish the needle as the aerosol precursor composition is vaporized by the needle. Note further that while example shapes and configurations of the resonant receiver coupling device and the transmitter coupling device are described herein, various other configurations and shapes may be employed.

FIG. 15 illustrates various operations in a method 1500 for assembling an aerosol delivery device, according to some example implementations. As illustrated in FIG. 15, the method may include providing a substrate comprising an aerosol precursor composition at operation 1502. The method may further include providing a resonant receiver coupling device at operation 1504. Additionally, the method may include positioning the substrate in proximity to the resonant receiver coupling device at operation 1506. The resonant receiver coupling device may be configured to be exposed to an oscillating magnetic field to heat the aerosol precursor composition to produce an aerosol.

In some implementations positioning the substrate in proximity to the resonant receiver coupling device at operation 1506 may comprise positioning the substrate in direct contact with the resonant receiver coupling device. Further, positioning the substrate in proximity to the resonant receiver coupling device at operation 1506 may include positioning the substrate inside the resonant receiver coupling device. The method may additionally include filling the substrate with the aerosol precursor composition. The aerosol precursor composition may comprise a liquid aerosol precursor composition.

The method may additionally include providing a transmitter coupling device and positioning the transmitter coupling device such that the transmitter coupling device at least partially surrounds the resonant receiver coupling device. Positioning the transmitter coupling device may include positioning the transmitter coupling device out of direct contact with the resonant receiver coupling device.

The method may additionally include forming a cartridge comprising the substrate and the resonant receiver coupling device. Further, the method may include forming a control body comprising the transmitter coupling device. Positioning the transmitter coupling device such that the transmitter coupling device at least partially surrounds the resonant receiver coupling device may include coupling the cartridge to the control body. Additionally, forming the control body may include coupling a power source to the transmitter coupling device.

FIG. 16 illustrates various operation in a method 1600 for aerosolization, according to some example implementations. As illustrated in FIG. 16, the method may include providing a cartridge at operation 1602. The cartridge may include an aerosol precursor composition and an atomizer. The method may additionally include providing a control body at operation 1604. The control body may include a power source and a wireless power transmitter. The method may further include directing current from the power source to the wireless power transmitter at operation 1606. Additionally, the method may include wirelessly heating the atomizer with the wireless power transmitter to heat the aerosol precursor composition to produce an aerosol at operation 1608.

Many modifications and other implementations of the disclosure will come to mind to one skilled in the art to which this disclosure pertains having the benefit of the teachings presented in the foregoing descriptions and the associated drawings. Therefore, it is to be understood that the disclosure is not to be limited to the specific implementations disclosed herein and that modifications and other implementations are intended to be included within the scope of the appended claims. Although specific terms are employed herein, they are used in a generic and descriptive sense only and not for purposes of limitation.

What is claimed is:

1. An aerosol delivery device comprising:
   a substrate configured to carry an aerosol precursor composition;
   a resonant transformer including a transmitter coupling device and a resonant receiver coupling device that is positioned in proximity to the substrate; and
   a pulse width modulation (PWM) inverter configured to drive the resonant transformer, the PWM inverter comprising:
      a bridge circuit coupled to the transmitter coupling device; and
      a PWM controller embodied as an integrated circuit and configured to output a PWM signal to the bridge circuit configured to drive the transmitter coupling device to generate an oscillating magnetic field and induce an alternating voltage in the resonant receiver coupling device when exposed to the oscillating magnetic field, the alternating voltage causing the resonant receiver coupling device to generate heat and thereby vaporize components of the aerosol precursor composition.

2. The aerosol delivery device of claim 1 further comprising a power source including a rechargeable supercapacitor, rechargeable solid-state battery or rechargeable lithium-ion battery, and configured to power the PWM inverter.

3. The aerosol delivery device of claim 2 further comprising a constant voltage regulator between the power source and PWM inverter, and configured to maintain a constant voltage level at the PWM inverter.

4. The aerosol delivery device of claim 1 further comprising a power source including a rechargeable supercapacitor, and configured to power the PWM inverter.

5. The aerosol delivery device of claim 4, wherein the power source further includes terminals connectable with a source of energy from which the rechargeable supercapacitor is chargeable.

6. The aerosol delivery device of claim 5, wherein the power source further comprises the source of energy, and the source of energy is or includes a rechargeable solid-state battery or rechargeable lithium-ion battery.

7. The aerosol delivery device of claim 1, wherein the bridge circuit is a half bridge composed of a pair of transistors and a pair of diodes.

8. The aerosol delivery device of claim 1 further comprising:
   a Hall effect current sensor positioned proximate the resonant receiver coupling device and configured to produce a measurement of an alternating current induced therein; and
   a microprocessor configured to receive the measurement and control operation of at least one functional element of the aerosol delivery device in response thereto.

9. The aerosol delivery device of claim 1 further comprising:
   a high-pass filter coupled to the resonant receiver coupling device, and configured to filter any direct voltage component from the alternating voltage induced in the resonant receiver coupling device; and
   a non-inverting amplifier circuit coupled to the high-pass filter, and configured to amplify the alternating voltage so filtered.

10. The aerosol delivery device of claim 1, wherein the transmitter coupling device is configured to at least partially surround the resonant receiver coupling device.

11. The aerosol delivery device of claim 10, wherein the transmitter coupling device defines a tubular or coiled configuration.

12. A control body coupled or coupleable with a cartridge that is equipped with a resonant receiver coupling device that is positioned in proximity to a substrate configured to carry an aerosol precursor composition, the control body comprising:
   a transmitter coupling device that with the resonant receiver coupling device forms a resonant transformer when the control body is coupled with the cartridge; and
   a pulse width modulation (PWM) inverter configured to drive the resonant transformer, the PWM inverter comprising:
      a bridge circuit coupled to the transmitter coupling device; and
      a PWM controller embodied as an integrated circuit and configured to output a PWM signal to the bridge circuit configured to drive the transmitter coupling device to generate an oscillating magnetic field and induce an alternating voltage in the resonant receiver coupling device when exposed to the oscillating magnetic field, the alternating voltage causing the resonant receiver coupling device to generate heat and thereby vaporize components of the aerosol precursor composition.

13. The control body of claim 12 further comprising a power source including a rechargeable supercapacitor, rechargeable solid-state battery or rechargeable lithium-ion battery, and configured to power the PWM inverter.

14. The control body of claim 13 further comprising a constant voltage regulator between the power source and PWM inverter, and configured to maintain a constant voltage level at the PWM inverter.

15. The control body of claim 12 further comprising a power source including a rechargeable supercapacitor, and configured to power the PWM inverter.

16. The control body of claim 15, wherein the power source further includes terminals connectable with a source of energy from which the rechargeable supercapacitor is chargeable.

17. The control body of claim 16, wherein the power source further comprises the source of energy, and the source of energy is or includes a rechargeable solid-state battery or rechargeable lithium-ion battery.

18. The control body of claim 12, wherein the bridge circuit is a half bridge composed of a pair of transistors and a pair of diodes.

19. The control body of claim 12, wherein the transmitter coupling device is configured to at least partially surround the resonant receiver coupling device.

20. The control body of claim 19, wherein the transmitter coupling device defines a tubular or coiled configuration.

* * * * *